United States Patent
Chen

(10) Patent No.: US 7,266,410 B2
(45) Date of Patent: *Sep. 4, 2007

(54) METHOD AND SYSTEM FOR THE PREDICTION OF CARDIAC ARRHYTHMIAS, MYOCARDIAL ISCHEMIA, AND OTHER DISEASED CONDITION OF THE HEART ASSOCIATED WITH ELEVATED SYMPATHETIC NEURAL DISCHARGES

(75) Inventor: Peng-Sheng Chen, Indianapolis, IN (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 47 days.

This patent is subject to a terminal disclaimer.

(21) Appl. No.: 11/069,753

(22) Filed: Feb. 28, 2005

(65) Prior Publication Data

US 2006/0004414 A1    Jan. 5, 2006

Related U.S. Application Data

(63) Continuation-in-part of application No. 10/882,645, filed on Jun. 30, 2004.

(51) Int. Cl.
*A61N 1/362* (2006.01)
*A61B 5/0402* (2006.01)

(52) U.S. Cl. .................. 607/3; 607/2; 607/4; 607/9; 600/508; 600/509; 600/515

(58) Field of Classification Search .............. 607/2–4, 607/9; 600/515, 508–509
See application file for complete search history.

(56) References Cited

U.S. PATENT DOCUMENTS 5,658,318 A *  8/1997  Stroetmann et al. ........... 607/6
6,272,377 B1 *  8/2001  Sweeney et al. ............ 600/515
6,521,462 B1 *  2/2003  Tanouye et al. ............ 436/149
6,885,888 B2 *  4/2005  Rezai .......................... 607/9

OTHER PUBLICATIONS

Akingba A G, Wang D, Chen P-S, Neves H, Montemagno C: Application of nanoelectrodes in recording biopotentials. Nanotechnology, 2003. IEEE-NANO 2003; 2:870-874.*
Swissa et al., Long-Term Subthreshold Electrical Stimulation of the Left Stellate Ganglion and a Canine Model Of Sudden Cardiac Death. J. Am. Coll. Cardiol. 2004; 43:858-64.*

* cited by examiner

*Primary Examiner*—Carl Layno
*Assistant Examiner*—Shevon Johnson
(74) *Attorney, Agent, or Firm*—Jones Day

(57) ABSTRACT

Methods and systems are provided for determining an increased likelihood of the occurrence of a cardiac arrhythmia, myocardial ischemia, congestive heart failure and other diseased conditions of the heart associated with elevated sympathetic neural discharges in a patient. The methods and systems comprise monitoring the sympathetic neural discharges of a patient from the stellate ganglia, the thoracic ganglia, or both, and detecting increases in the sympathetic neural discharges. The methods and systems may further comprise delivering therapy to the patient in response to a detected increase in the sympathetic neural discharge, such as delivering one or more pharmacological agents; stimulating myocardial hyperinnervation in the sinus node and right ventricle of the heart of the patient; and applying cardiac pacing, cardioversion or defibrillation shocks. Pharmacologic agents which may be used in connection with the delivery of include those which are known to exert anti-arrhythmic effect and anti-convulsant agents, such as phenytoin, carbamazepine, valproate, and phenobarbitone. Other pharmacologic agents may be used to treat impending myocardial ischemia and other diseased conditions of the heart associated with elevated sympathetic neural discharges.

39 Claims, 19 Drawing Sheets

FIG. 3A
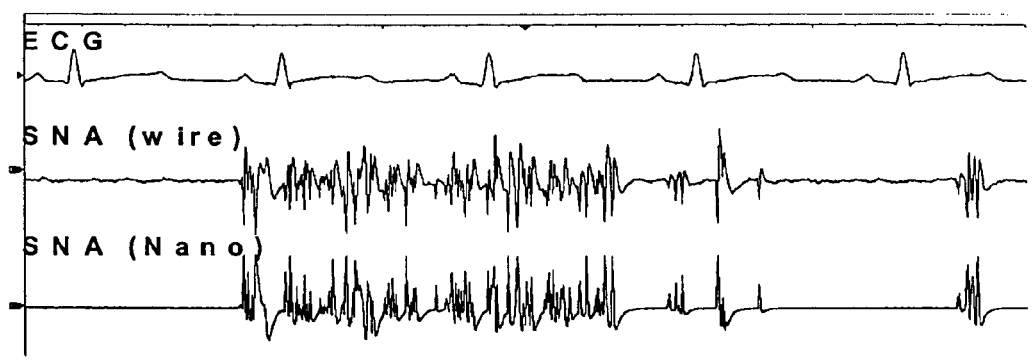
FIG. 3B
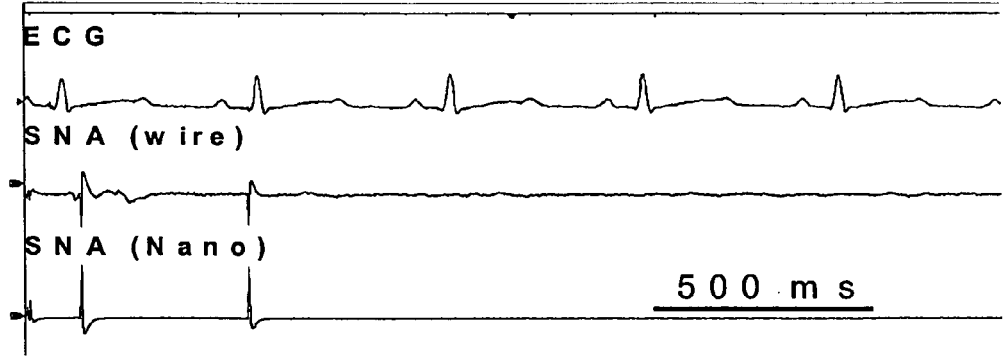
FIGURE 3

FIG. 8A
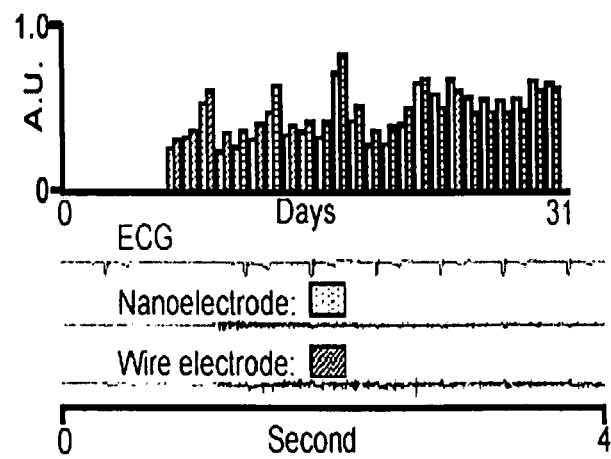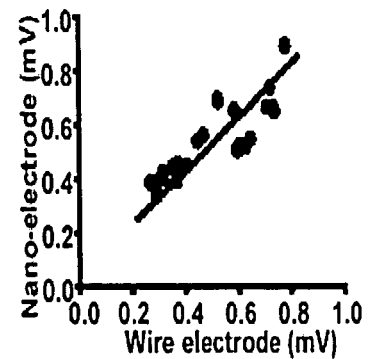
FIG. 8B
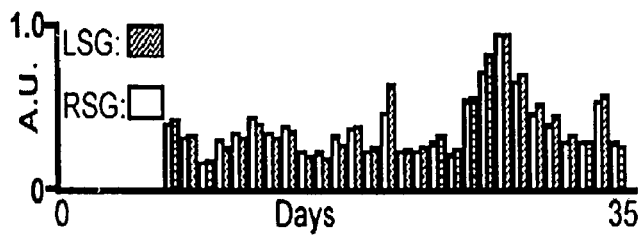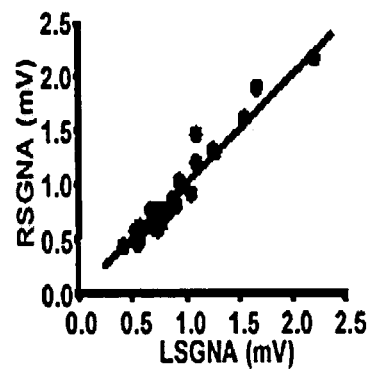
FIG. 8C
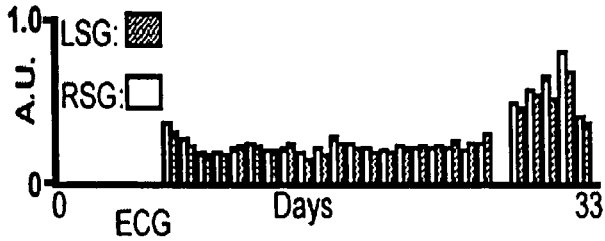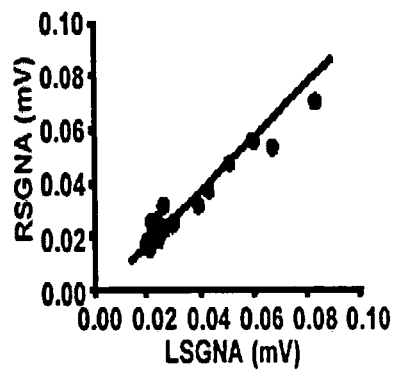
FIGURE 8

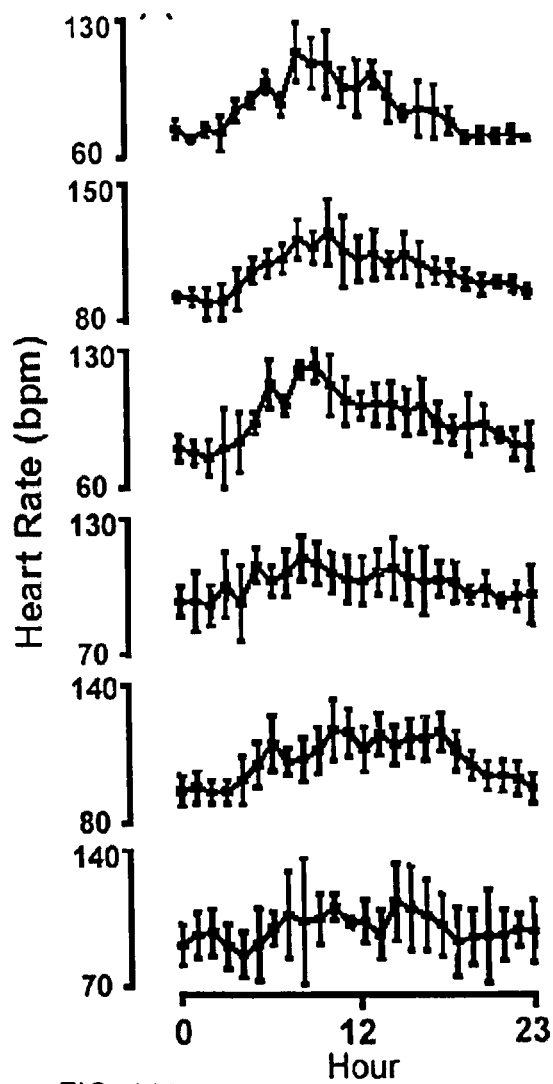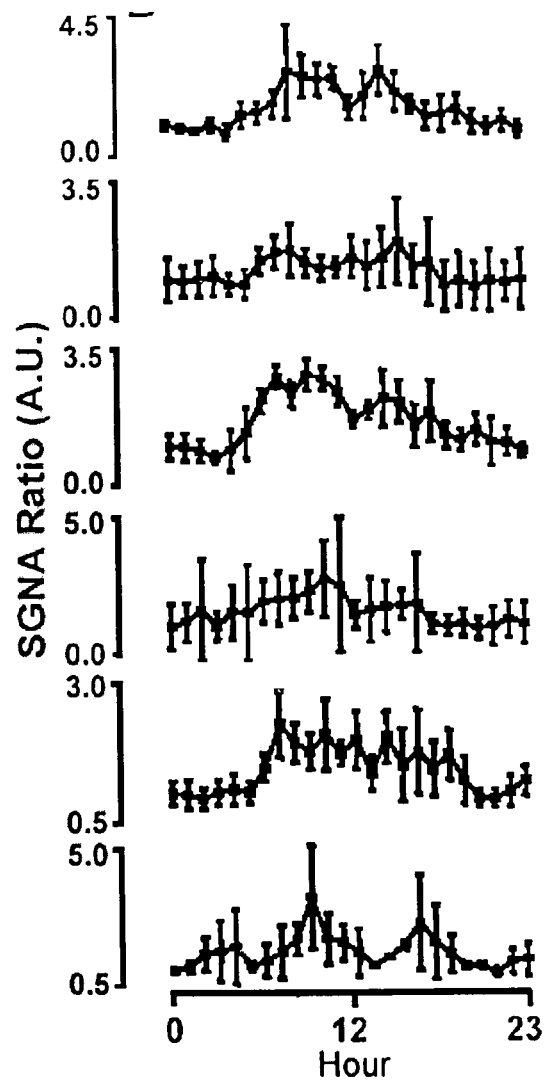
FIG. 11A
FIG. 11B
FIGURE 11

METHOD AND SYSTEM FOR THE PREDICTION OF CARDIAC ARRHYTHMIAS, MYOCARDIAL ISCHEMIA, AND OTHER DISEASED CONDITION OF THE HEART ASSOCIATED WITH ELEVATED SYMPATHETIC NEURAL DISCHARGES

CROSS-REFERENCE TO RELATED APPLICATIONS

This is a continuation-in-part application of co-pending application Ser. No. 10/882,645, filed Jun. 30, 2004, the entirety of which is incorporated by reference.

GOVERNMENT INTEREST

This invention was made in part with government support under Grant R01 HL66389, awarded by the National Institutes of Health. The government has certain rights to this invention.

FIELD OF THE INVENTION

The invention generally relates to a methods and systems for the prediction of cardiac arrhythmias of the type that can result in sudden cardiac death.

BACKGROUND OF THE INVENTION

Sudden cardiac death (SCD) is a major public health problem that accounts for more than half of all cardiovascular deaths. SCD takes the lives of approximately 450,000 people in the United States each year, more than lung cancer, breast cancer, stroke, and AIDS combined. Most cases of SCD are due to ventricular arrhythmias and there is often an element of underlying ischemic heart disease. Ventricular tachycardia (VT) and ventricular fibrillation (VF) are different types of ventricular arrhythmias. VT is an abnormally fast ventricular heart rhythm which is, by itself, typically not fatal. VF is a chaotic ventricular heart rhythm which produces little or no net blood flow from the heart, such that there is little or not net blood flow to the brain and other organs. VF, if not terminated, results in death. Patient groups most at risk of ventricular arrhythmias leading to SCD include those with an acute or chronic myocardial infarction. Accordingly, deaths from SCDs may be lowered by preventing the specific heart rhythm disturbances (ventricular arrhythmias) associated with it.

Different treatment options exist for SCD. The most common treatment includes implantable cardiac defibrillators (ICD) and drug therapy. ICDs have been available in the United States since the mid-1980s and have a well-documented success rate in decreasing the rate of death of patients at high risk for SCD. A major trial conducted by the U.S. National Institutes of Health (the Anti-arrhythmics Versus Implantable Defibrillator or AVID trial) compared therapy with the best available anti-arrhythmic drugs with ICD therapy for patients with spontaneous ventricular tachycardia or ventricular fibrillation. The overall death rate in the ICD patient group was found to be 39% lower than the death rate of patients treated with anti-arrhythmic drugs after only 18 months mean follow-up.

An ICD has two basic components: the ICD generator and the lead system for pacing and shock delivery to which it is connected. An ICD generator contains sensing circuits, memory storage, capacitors, voltage enhancers, a telemetry module, and a control microprocessor. Advances in miniaturization and complexity in all of these components have permitted a tremendous reduction in size of the generator itself despite increased functionality, such as added programming options, anti-tachycardia pacing, single- and dual-chamber rate-responsive pacing for bradycardia, biphasic defibrillation waveforms, enhanced arrhythmia detection features, and innovations in lead systems.

Current ICD technology, however, provides for the detection and recognition of an arrhythmia based on the sensed heart rate once it has already started. This leaves very little time to protect the individual from death resulting from SCD. Although there have been several attempts at developing new technology for predicting the onset of a cardiac arrhythmia, many of these methods and systems appear to rely primarily on events occurring within the heart, such as sensed heart rate and electrocardiography (ECG). For example, U.S. Pat. No. 6,308,094 discloses a method and device for predicting cardiac arrhythmias by gathering and processing electrocardiographic data, such as intervals between heart beats (RR-series) or other heart signals, to predict the occurrence of a cardiac arrhythmia. U.S. Pat. No. 6,516,219 discloses a method and apparatus for forecasting arrhythmia based on real-time intact intracardiac electrograms.

SUMMARY OF INVENTION

Methods and systems are provided for determining an increased likelihood of the occurrence of a cardiac arrhythmia, myocardial ischemia, and/or other diseased condition of the heart associated with elevated sympathetic nerve discharges in a patient. The methods and systems disclosed herein generally comprise monitoring the sympathetic neural discharges of a patient from the stellate ganglia, the thoracic ganglia, and/or any other sympathetic nerve identified as having an influence over the heart rate of a patient. Other sympathetic nerves suitable for use in connection with the prediction of cardiac arrhythmias may be generally determined by obtaining simultaneous recordings of neural discharges and heart rate in a test subject and determining whether there exists a correlation between an observed increase in the amplitude and/or frequency of the neural discharges and an increase in heart rate.

Elevated stellate ganglia nerve activity (SGNA) has been demonstrated to precede the onset of cardiac arrhythmias of the type leading to SCD and, additionally, myocardial ischemia. Myocardial ischemia may or may not cause chest pain (angina). When myocardial ischemia does not cause chest pain, it is known as "silent ischemia." It has been shown that stellate ganglion stimulation can cause ischemia, as shown by the ST segment elevation in FIG. 12C. The ST elevation suggest that significant myocardial ischemia, probably due to the combined effects of alpha-receptor induced coronary constriction and beta-receptor increase in oxygen consumption. The ability to continuously monitor SGNA will provide a method to predict the onset of silent ischemia.

In one embodiment, the sympathetic neural discharges may be monitored by a sensor or electrode that is implanted in the stellate ganglia to measure the stellate ganglia nerve activity (SGNA) of the patient from the left stellate ganglion (LSG), the right stellate ganglion (RSG), or both. For example, the electrode may directly sense electrical activity of the stellate ganglia and transmit this data to a processor. The processor may then analyze the data acquired from the electrode and, upon the determination that the SGNA has increased beyond a defined normal value, produce an output signal indicating the likely onset of an arrhythmia, myocardial ischemia, and/or other diseased condition of the heart associated with elevated sympathetic nerve discharges.

In another embodiment, an increase in the sympathetic neural discharge in the patient may be determined by comparing the parameters for the sensed and normal sympathetic neural discharges in the patient. In yet another embodiment, an increase in the sympathetic neural discharge may be determined by detecting increases in the amplitude and frequency of the sensed sympathetic neural discharge beyond defined normal values, such as the sensed electrical activity of the stellate ganglia and/or the thoracic ganglia.

The defined normal value represents a value above or beyond which is indicative of an impending arrhythmic, ischemia or other diseased condition of the heart associated with elevated sympathetic nerve discharges and may be determined with reference to the normal baseline sympathetic neural discharge. For example, a two-fold or greater increase in the amplitude of the sensed sympathetic neural discharge from the normal baseline amplitude of sympathetic neural discharge may be used as a suitable defined normal value. A second defined normal value reflecting the frequency of the sympathetic neural discharge above or beyond which is indicative of an impeding arrhythmic condition of the heart may similarly be provided. The defined normal values may be preset or user-defined programmable values.

An output signal may be generated in response to a determined increase in the sympathetic neural discharge. In one embodiment, the output signal may be an audible sound, a radio-transmitted signal, or any other type of signal that would alert the patient or physician to the possibility of an impending arrhythmia. In another embodiment, the output signal may be an analog or digital command signal directing the delivery of therapy to the patient.

Suitable therapy for use in connection with the methods and systems are known in the art and may include any one or a combination of the following: delivering one or more pharmacological agents; stimulating myocardial hyperinnervation in the sinus node and right ventricle of the heart of the patient; and applying cardiac pacing, cardioversion or defibrillation shocks, to name a few.

Any one or more pharmacologic agent(s) may be used in connection with the delivery of therapy. Such pharmacologic agents may include those which are effective in treating cardiac arrhythmias, myocardial ischemia, congestive heart failure, and any other diseased condition of the heart that is associated with elevated sympathetic neural discharges. Pharmacologic agents which may be used in connection with the delivery of anti-arrhythmic therapy may include, but are not limited to, those which are known to exert anti-arrhythmic effect, such as sodium channel blockers, β-blockers, potassium channel blockers, such as amiodarone and solatol, and calcium channel blockers, such as verapamil and diltiazem. Pharmacologic agents suitable for the treatment of myocardial ischemia may include, but are not limited to, statins, angiotensin-converting enzyme (ACE) inhibitors, aspirin, beta blockers, calcium channel blockers, and nitrates. Other suitable pharmacologic agents may include anti-convulsant agents, including but not limited to phenytoin, carbamazepine, valproate, and phenobarbitone, to name a few, which are believed to have anti-arrhythmic effect.

The methods and systems described herein may be incorporated into any number of implantable medical devices including, but not limited to, implantable cardiac rhythm management systems such as pacemakers, cardioverters, defibrillators, and the like. The present methods and systems may also be incorporated in external unimplanted devices of the same sort, as well as in external monitors, programmers and recorders.

The above and other objects, features and advantages will become apparent to those skilled in the art from the following description of the preferred embodiments.

BRIEF DESCRIPTION OF THE DRAWINGS

FIG. 3 depicts simultaneous recordings of (a) renal sympathetic neural discharges obtained from a wire electrode and a nanoelectrode and (b) electrocardiograph (ECG) recordings obtained from a rabbit subject over a time span of 2 seconds. FIG. 3A shows the bursts of renal sympathetic neural discharges and FIG. 3B shows suppression of renal sympathetic neural discharges by intravenous bolus dose of xylazine and ketamine.

FIG. 5A shows the onset of increased SGNA at time (a) which was followed by an increase in heart rate. FIG. 5B shows the increase in amplitude of the SGNA signals at (b) which is followed but further increases in heart rate. FIG. 5C shows burst increases in the amplitude of SGNA signals at (c), (d), (e), (f), (g), and (h), all of which were followed by short runs of increased atrial rate.

FIGS. 8A-C show the SGNA obtained from stainless steel wire electrodes implanted in the LSG and RSG of an ambulatory normal canine subject. FIG. 8A shows significant correlation between SGNA recorded from the nanoelectrode and from the stainless steel wire electrode from the LSG of an ambulatory normal canine subject. An example of the actual SGNA recordings from the nanoelectrode and wire electrode is shown at the bottom of the bar graph. FIGS. 8B and 8C show significant correlation between the SGNA obtained from a stainless steel wire electrode implanted in the LSG and the RSG in two ambulatory normal canine subjects. Each column in the bar graph and each dot in the corresponding X-Y graph show the average SGNA over a one-day period. The SGNA amplitude remained stable or slightly increased with time. These figures demonstrate that SGNA may be adequately recorded using either the nanoelectrode array or the stainless steel wire electrode.

FIG. 9A is the baseline recording showing no SGNA (from either LSG or RSG) and an ECG showing slow heart rate with significant sinus arrhythmia. FIG. 9B shows increased SGNA from the LSG and sporadic SGNA from the RSG during increased heart rate. FIG. 9C shows sporadic SGNA from the LSG and increased SGNA from the RSG during increased heart rate. FIG. 9D shows increased bilateral SGNA (from the LSG and RSG) associated with rapid heart rate. FIG. 9E shows the onset of bilateral SGNA (as indicated by the arrows) during rapid heart rate. A gradual heart rate deceleration is indicated by the asterisk. A stainless steel wire electrode was used to obtain the SGNA recordings.

FIGS. 10A-C are continuous recordings obtained from an ambulatory normal canine subject fifteen (15) days after implantation of the stainless steel wire electrode. In FIG. 10A, the increase in SGNA at (a) was followed by an increase in heart rate. In FIG. 10B, further increases in SGNA at (b) resulted in further increases in heart rate. In FIGS. 10C-D, brief bursts of SGNA at (c) were followed by immediate acceleration in heart rate. The arrows point to possible motion artifacts. FIG. 10E show the relationship between SGNA and blood pressure at baseline (d), unilateral increase in SGNA from the RSG at (e) and bilateral increase in SGNA from both the LSG and RSG at (f). Again, a stainless steel wire electrode was used to obtain the SGNA recordings.

FIGS. 11A-B show average heart rate and normalized SGNA, respectively, over a 24 hour period. The SNGA was normalized to a midnight value.

FIGS. 12A and B show the effect of electrical stimulation on the LSG and RSG, respectively and FIG. 12C shows baseline ST elevation immediately after electrical stimulation of the RSG.

FIG. 14A shows persistent SGNA (as indicated by the horizontal line over the SGNA) from the LSG followed by the onset of ventricular tachycardia (VT). FIG. 14B shows intermittent increases in SGNA from the LSG (as indicated by the arrows) also followed by VT. The asterisk shows signal drop probably due to movement of the canine subject.

FIG. 16A shows pacemaker non-capture, resulting in the conversion of intermittent SGNA into continuous SGNA in FIG. 16B. The SGNA continued uninterrupted for 6 minutes, resulting in accelerated ventricular escape rhythm followed by ventricular fibrillation, as shown in FIG. 16C. FIGS. 16A-B are continuous tracings.

DESCRIPTION OF THE PREFERRED EMBODIMENTS

Figure 1:
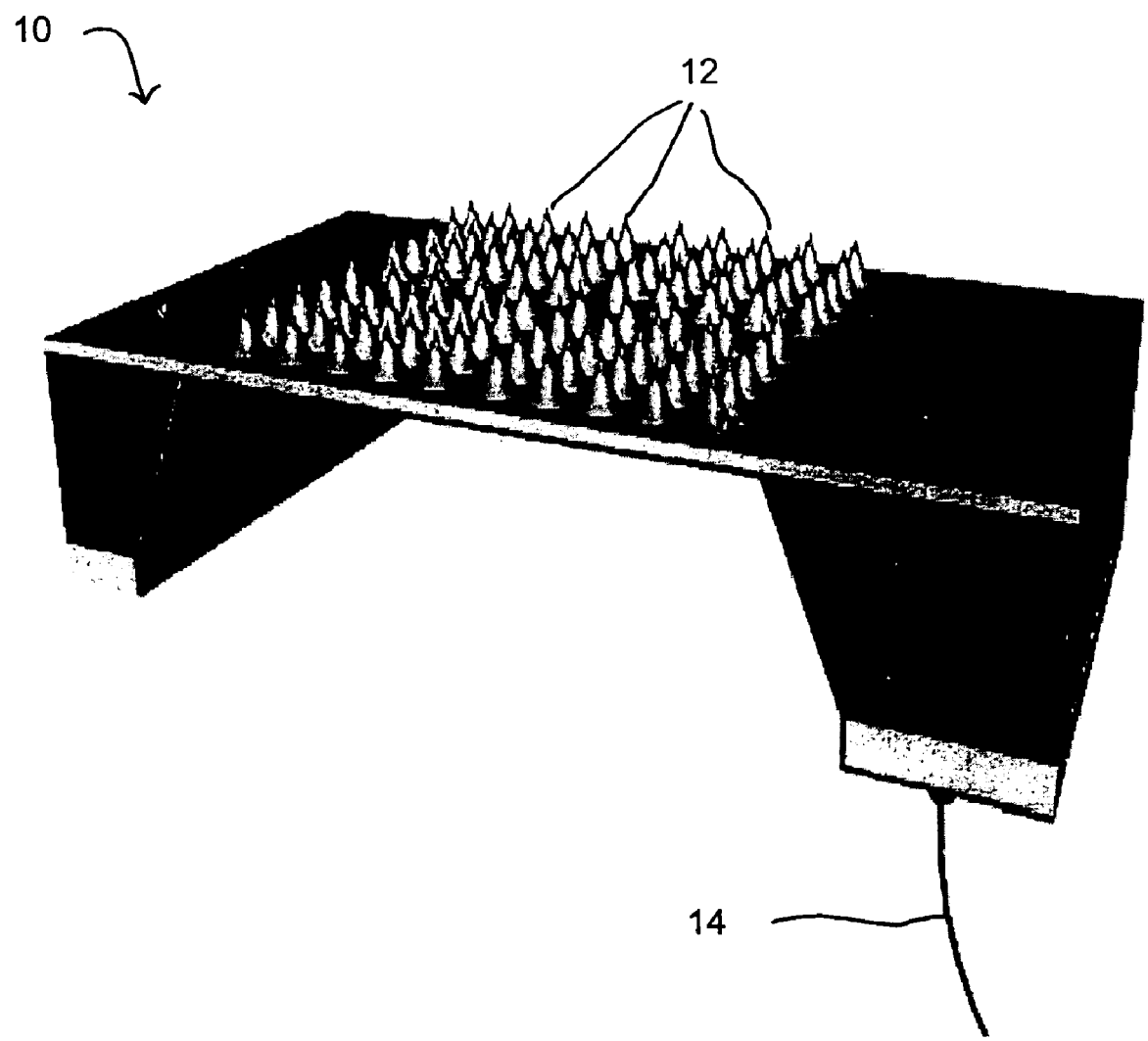
FIG. 1 is a perspective view of a nanoelectrode array.

Methods and systems are disclosed for determining an increased likelihood of the occurrence of a cardiac arrhythmia, myocardial ischemia, congestive heart failure, and any other diseased condition of the heart in a patient that is associated with elevated sympathetic neural discharges. The methods and systems disclosed herein comprise monitoring the sympathetic neural discharges of a patient; determining an increase in the sympathetic neural discharges in the patient beyond defined normal values; and producing an output signal upon a determined increase in the sympathetic neural discharges in the patient. In one embodiment, the output signal may be an audible sound, a radio-transmitted signal, or any other type of signal that would alert the patient or physician to the possibility of an impending arrhythmia or other diseased conditions of the heart. In another embodiment, the output signal may be a command signal directing the delivery of suitable therapy.

The sympathetic neural discharges of a patient may be monitored by a sensor or electrode that is implanted in the stellate ganglia, the thoracic ganglia, and/or any other sympathetic nerve for which the rate of neural discharge influences the heart rate in a patient. The sensor or electrode may directly sense electrical activity of the stellate ganglia, the thoracic ganglia or other suitable sympathetic nerve of the patient and transmit this data to a processor for immediate processing or to a memory for storage.

In a preferred embodiment, sympathetic nerve recordings obtained from the stellate ganglia, the thoracic ganglia, or both. Increased neural discharges from the stellate ganglia has been observed to precede the onset of cardiac arrhythmias. Consistent with this observation, partial or complete ablation of the LSG, together with the thoracic ganglia T2 to T4, was demonstrated to be effective in reducing the incidence of SCD in patients after a first myocardial infarction. Schwartz P J, et al. Left cardiac sympathetic denervation in the management of high-risk patients affected by the long-QT syndrome. *Circulation*. 2004; 109:1926-1833. These findings suggest that the LSG and the thoracic ganglia are important for ventricular arrhythmogenesis and SCD among high risk patients.

Indeed, it has previously been found that simulation of the LSG has been found to result in a significant increase in incidence of ventricular arrhythmias and SCD in canine subjects. In contrast, stimulation of the RSG has been shown to be anti-arrhythmic. A method for inducing ventricular arrhythmias in an animal model is disclosed in U.S. Pat. No. 6,351,668, which is incorporated herein in its entirety. Such an animal model is useful in collecting data pertinent to predictors of heart arrhythmias and for testing techniques intended to predict the onset of heart arrhythmias, the disclosures for which are provided in U.S. Pat. Nos. 6,353,757 and 6,398,800, which are incorporated herein in their entirety.

Previous studies have demonstrated heterogeneous sympathetic hyperinnervation in the left ventricle in canine models for sudden cardiac death. Cao J-M, Chen L S, KenKnight B H et al. Nerve sprouting and sudden cardiac death. Circ. Res. 2000; 86:816-21. The electrical heterogeneity does not have significant clinical consequences in normal hearts. However, when the ion channels in the heart are altered by either genetic mutations or electrical remodeling after a myocardial infarction and atrioventricular block, this heterogeneity may be amplified and cause arrhythmia. Accordingly, different sympathetic nerves may exert very different effects on the heart rate.

For example, increased neural discharges from the LSG exert an anti-arrhythmic effect, whereas increased neural discharges from the RSG is believed to be anti-arrhythmic. It has been demonstrated that electrical stimulation of the left stellate ganglia in canine subjects induce high magnitude cardiac nerve sprouting and increased ventricular sympathetic nerve density. If the canine subjects also have complete atrioventricular block and myocardial infarction, sub-threshold electrical stimulation of left stellate ganglia resulted in a high yield canine model of sudden cardiac death. In contrast, sub-threshold electrical stimulation of the right stellate ganglia may induce nerve sprouting from the right stellate ganglia and thereby reduce the risk of SCD in canine subjects with augmented nerve sprouting, myocardial infarction and complete atrioventricular block.

Sub-threshold electrical stimulation to the left stellate ganglia was administered in six (6) normal canine subjects and six (6) canine subjects with myocardial infarction and complete atrioventricular block. The threshold current is the minimum amount of current needed to induce increases in blood pressure and heart rate. All twelve (12) canine subjects were monitored with either an ICD or with a DSI transmitter implanted in a sub-muscular chest pocket for continuous recording with a sampling rate of 1,000 per second. The hearts were harvested a month later. All hearts showed significant hypertrophy, nerve sprouting and sympathetic hyperinnervation. The canine subjects with myocardial infarction and complete atrioventricular block demonstrated frequent ventricular tachycardia and a high incidence of sudden cardiac death. These results show that sub-threshold electrical stimulation to the LSG induces cardiac nerve sprouting and sympathetic hyperinnervation, and facilitates the development of a high-yield canine model of ventricular arrhythmia and sudden cardiac death.

In one embodiment, the sensor or electrode may be a nanoelectrode array. As shown in FIG. 1, the nanoelectrode array (10) comprising a plurality of nanoelectrodes (12). The signals from the sympathetic neural discharges are received by each of the nanoelectrodes, combined before digitization and transmitted by a single electrical wire (14). In a preferred embodiment, each individual nanoelectrode has a sharp tip of approximately 10 to 50 nm in diameter and is configured to penetrate the epineurium or the connective tissue sheath that surrounds the sympathetic nerve bundle without damaging the nerves and surrounding blood vessels. Akingba A G, Wang D, Chen P-S, Neves H, Montemagno C: Application of nanoelectrodes in recording biopotentials. Nanotechnology, 2003. IEEE-NANO 2003; 2:870-874

Figure 2:
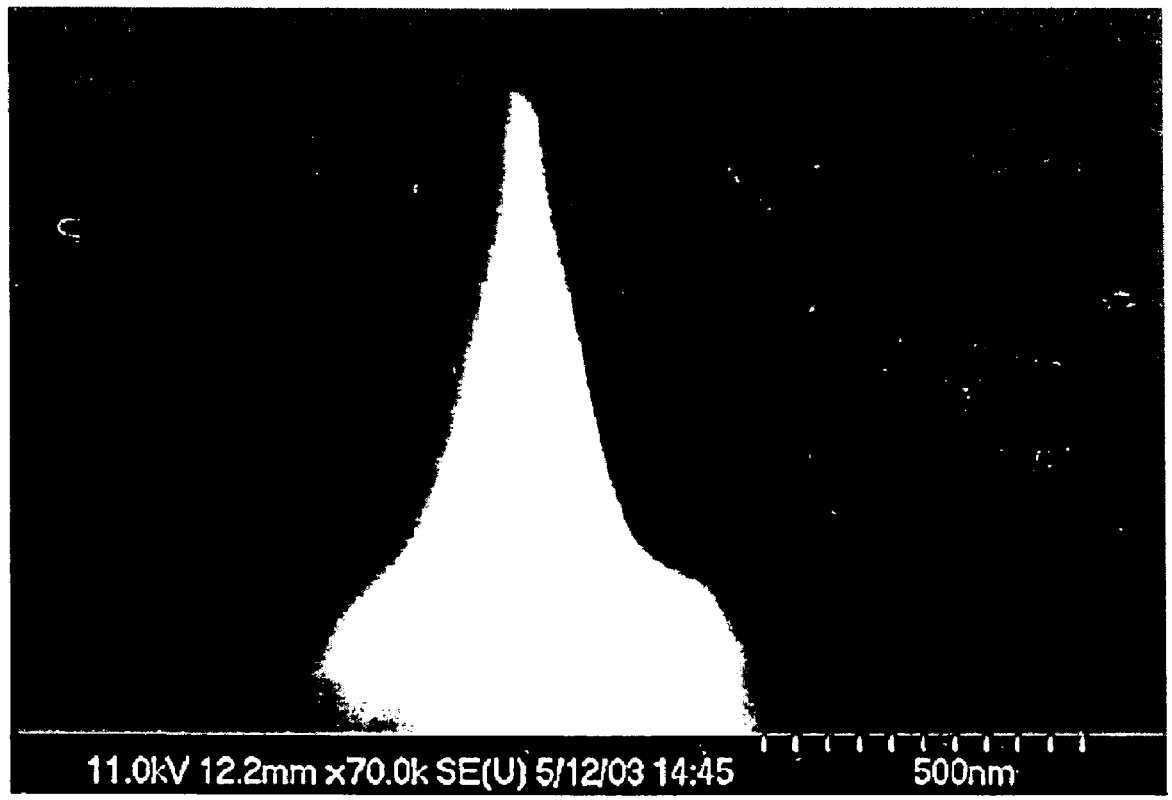
FIG. 2 is a magnified view of an individual tip from a nanoelectrode array.

FIG. 2 depicts an individual nanoelectrode from the nanoelectrode array having a diameter of approximately 50 nm. The tips of the nanoelectrode are placed directly on the LSG to record the sympathetic neural discharges. A nanoelectrode array provides the benefit of providing increased surface contact with the nervous tissue and improved signal-to-noise ratio.

Data acquired from the sensor or electrode may be filtered to produce optimal signal-to-noise ratio. The amplitude of a signal from a sympathetic nerve is typically −35 to +35 μV and the electrode noise is on average 10 μV for an ideal electrode resistance between 100 kΩ and 10 MΩ at 37° C. for a bandwidth of 1 kHz. Much of the noise during in vivo recording results from the interfacial effects between the neuron, epineurium, electrolyte and the electrode, which is dominated by the charge transfer resistance and the coupling resistance. Cross-talk from parasitic capacitances may also result in the generation of unwanted signals when using conventional electrodes to record sympathetic neural discharges.

Wide band pass filter (1 to 3000 Hz) allows recording of sympathetic neural discharges but also allows for a significant amount of noise generated by cardiac and respiratory related movement artifacts. A greater high pass filter setting (30 to 100 Hz) removes some of the noise and achieves a more stable baseline of the recorded sympathetic neural discharge signals.

The data acquired from the sensor or nanoelectrode may be continuously monitored to detect increases in the sympathetic neural discharges. In one embodiment, an increase in the sympathetic neural discharges in the patient may be determined by detecting an increase in the amplitude and frequency of the sensed sympathetic neural discharges beyond defined normal values. In another embodiment, an increase in the sympathetic neural discharges in the patient may be determined by comparing the parameters for the sensed sympathetic neural discharges in the patient with the parameters defined for normal sympathetic neural discharges.

In an alternative embodiment, a wire electrode may be used to obtain SGNA recordings. SGNA recordings have been successfully obtained from the LSG, RSG, and vagal nerves implanting the stainless steel wires connected to the transmitter directly under the fascia of the stellate ganglia. A high degree of concordance between SGNA signals registered by the nanoelectrode array and by the stainless steel wires has been demonstrated. FIG. 8 depicts the correlation between SGNA recorded by nanoelectrode and the wire electrode from the LSG of a canine subject. An example of the actual left SGNA recordings from the nanoelectrode and the wire electrode is shown at the bottom of the bar graph. FIG. 8 demonstrates that SGNA may be adequately recorded using either the nanoelectrode array or the stainless steel wire electrode.

The defined normal value represents a value above and beyond which is indicative of an impending arrhythmic condition of the heart and may be determined with reference to the normal baseline sympathetic neural discharge. For example, a two-fold or greater increase in the amplitude of the sensed sympathetic neural discharge from the normal baseline amplitude of sympathetic neural discharge may be used as a suitable defined normal value. A second defined normal value with respect to the frequency of the sympathetic neural discharge may be similarly provided. The defined normal values may be a preset or user-defined programmable value.

Once an increase in the sympathetic neural discharges has been determined, an output signal may be generated. In one embodiment, the output signal may be an audible sound, a radio-transmitted signal, or any other type of signal that would alert the patient or physician to the possibility of an impending arrhythmia or other diseased condition of the heart associated with elevated sympathetic neural discharge. Upon the generation of the output signal, the patient or physician may then take precautionary or therapeutic measures to avoid or reduce the likelihood of an impending cardiac arrhythmia or other diseased condition of the heart.

In another embodiment, the output signal may be a command signal directing the delivery of suitable therapy. Suitable therapy for use in connection with the methods and systems are known in the art and may include any one or a combination of the following: delivering one or more pharmacological agents; stimulating myocardial hyperinnervation in the sinus node and right ventricle of the heart of the patient; and cardiac pacing, cardioversion, or defibrillation shocks. A suitable drug delivery system for an implantable cardiac device is disclosed in U.S. Pat. No. 6,361,522, which is incorporated herein in its entirety.

Pharmacologic agents may include those which are known to exert an anti-arrhythmic effect, such as sodium channel blockers, β-blockers, potassium channel blockers, such as amiodarone and solatol, and calcium channel blockers, such as verapamil and diltiazem.

Other suitable anti-arrhythmic pharmacologic agents include anti-convulsant agents, such as phenytoin, carbamazepine, valproate, and phenobarbitone. The LSG is capable of high frequency neuronal discharges and these discharges directly increase heart rate. Anti-convulsants work by selectively suppressing high frequency neuronal discharges in the central and peripheral nervous system. Anti-convulsants are also known to suppress cardiac sympathetic nerve discharges. Because of the importance of the autonomic nervous system in arrhythmogenesis, drugs that prevent the release of adrenergic neurotransmitters may thereby decrease the sympathetic outflow are useful for controlling cardiac arrhythmia.

It has been shown, for example, that phenytoin can also be used to suppress cardiac arrhythmia induced by digitalis toxicity. The action of phenytoin is related to use- and frequency-dependent selective suppression of high-frequency neuronal activity. The molecular mechanism for this is a voltage-dependent blockade of membrane sodium channels responsible for the action potential. Through this action, phenytoin obstructs the positive feedback that underlies the development of maximal seizure activity.

Anti-convulsants may block the sympathetic nerve discharges through two actions. One is frequency-dependent block of sodium currents and the second is a block of calcium currents. A combined channel blockade may account for the effects of anticonvulsant drugs. In addition to epilepsy, anti-convulsants, such as phenytoin and carbamazepine, are also useful in treating neuropathic pain, which is characterized by abnormal spontaneous and increased evoked activity from damaged areas of the peripheral nervous system.

Other suitable pharmacologic agents may also be used for the treatment of myocardial ischemia and may include, but are not limited to, statins, angiotensin-converting enzyme (ACE) inhibitors, aspirin, beta blockers, calcium channel blockers, and nitrates. Any other suitable pharmacologic agent, that is known to treat a diseased condition of the heart associated with elevated sympathetic neural discharges, may be used in combination with any other pharmacologic agent and/or therapy.

Anti-arrhythmic therapy may also be administered by stimulating myocardial hyperinnervation in the sinus node and right ventricle of the heart of the patient by applying electrical stimulation to the RSG of the patient or by applying Nerve Growth Factor or other neurotropic substances to the RSG, as disclosed in U.S. Pat. No. 6,487,450, which is incorporated herein in its entirety.

The methods disclosed herein may be carried out by a programmable implantable or external device, including, but not limited to, implantable cardiac rhythm management systems such as pacemakers, cardioverters, ICDs, and the like. In one embodiment, the system may comprise a microprocessor, memory, bi-directional data bus, a sympathetic nerve activity (SNA) sensing unit, an output unit and a telemetry interface.

The microprocessor may communicate with the memory through the data bus and execute the program stored in the memory. The microprocessor may include a comparator, such as a summing amplifier, operation amplifier, or other methods of comparing the levels of analog voltage signals. Furthermore, if the sensors or the electrodes produce digital values reflecting the sympathetic neural discharges, then numerous methods known to one of skill in the art may be utilized to digitally compare the respective sympathetic neural discharges.

The memory may comprise any suitable combination of read-only memory (ROM) containing the device operating software, random access memory (RAM) for data storage, and on-board or off-board cache memory associated with the microprocessor. The data bus permits communication between the microprocessor, memory, SNA sensing unit, output unit and the telemetry interface. The telemetry interface may be used for downloading stored data to an external programmer and for receiving telemetry from the programmer to modify programmable parameters and/or change the device operating software.

The SNA sensing unit may comprise one or more electrodes or sensors coupled to sympathetic nerves of the patient, such as the LSG, and interface circuits that receive and process the sensed signals from the electrodes. Accordingly, the SNA sensing unit may receive electrical signals from the sympathetic nerves of the patient, filter those signals, and convert them into digital data or otherwise make the data available to the microprocessor.

Accordingly, in one embodiment, the microprocessor may instruct the SNA sensing unit to collect data from the sympathetic nerve, which is then transmitted over bus to the microprocessor for immediate processing or to the memory for storage and subsequent processing as appropriate. The microprocessor may then execute the programming resident in memory to identify increases in the sympathetic neural discharges of the patient and command the output unit to produce an output signal in response thereto.

The methods and systems illustrated with reference to the drawings and described herein are merely illustrative of the principles of the invention which may be implemented in alternative embodiments to achieve other ends than those specifically described herein. Accordingly, the following examples are set forth for the purpose of illustration only and are not construed as limitations on the method disclosed herein.

EXAMPLE 1

Rabbit Renal Sympathetic Nerve Recordings

A standard wire electrode and a nanoelectrode array was implanted on the renal sympathetic nerve of a New Zealand white rabbit. Simultaneous recordings of the ECG and renal sympathetic neural discharges were obtained. The renal sympathetic neural discharges was recorded with both a standard wire electrode and a nanoelectrode array and amplifier. The signals were digitized with a band pass filter of 30 to 500 Hz and a digitization rate of 1 K/sec.

FIG. 3 shows the ECG and renal sympathetic neural discharge recordings obtained from the rabbit. The nanoelectrode recordings provided a lower baseline noise than the wire electrode and therefore a higher signal-to-noise ratio. FIG. 3A shows bursts of renal sympathetic neural discharges, which did not correlate with changes in the heart rate. FIG. 3B shows the suppression of renal sympathetic neural discharges by intravenous bolus dose of xylazine and ketamine.

EXAMPLE 2

Sympathetic Neural Discharges of the Left Stellate Ganglion and Heart Rate Control The relationship between the SGNA of the LSG and the heart rate was investigated in a normal canine subject. A normal canine subject was anesthetized with isofluorane and the chest was opened at the third intercostal space. The LSG was identified and a nanoelectrode was implanted under the fibrous capsule. The fibrous capsule was then closed with a 4-0 silk suture and additional sutures were placed on the wire to secure the nanoelectrodes. The nanoelectrodes were then connected to a DSI transmitter (DSI TL 10M3-D70-EEE, Data Sciences, International) with a low pass filter of 250 Hz and a digitization rate of 1 K/sec. An additional bipolar channel of the DSI transmitter was used for ECG recordings between the right and left chest. All recordings shared a common ground.

Figure 4:
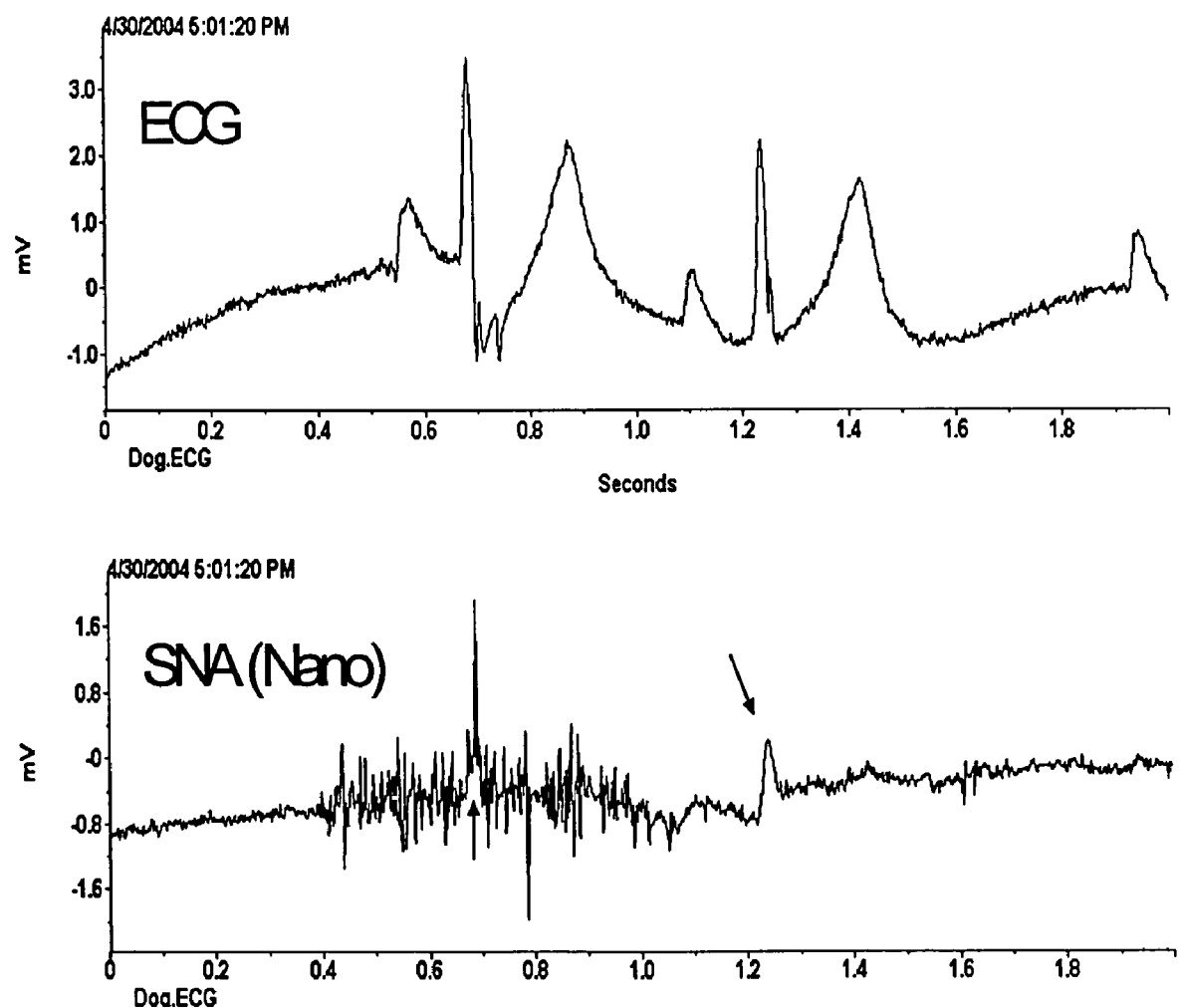
FIG. 4 depicts simultaneous recordings of ECG and SGNA from the LSG of an ambulatory normal canine subject two weeks after implantation of the nanoelectrode to the LSG. A burst of SGNA preceded the onset of accelerated atrial rate by approximately 0.2 seconds. The arrow indicate cross-talk from the surface ECG, which shared the same ground as the nanoelectrode.

FIG. 4 shows the relationship between the SGNA of the LSG and heart rate in an ambulatory normal canine subject two weeks after implantation of the nanoelectrode in the LSG. Bursts of SGNA preceded the onset of accelerated atrial rate by approximately 200 ms (0.2 seconds). The arrow points to cross-talk from the surface ECG, which shared the same ground as the nanoelectrode.

Figure 5A:
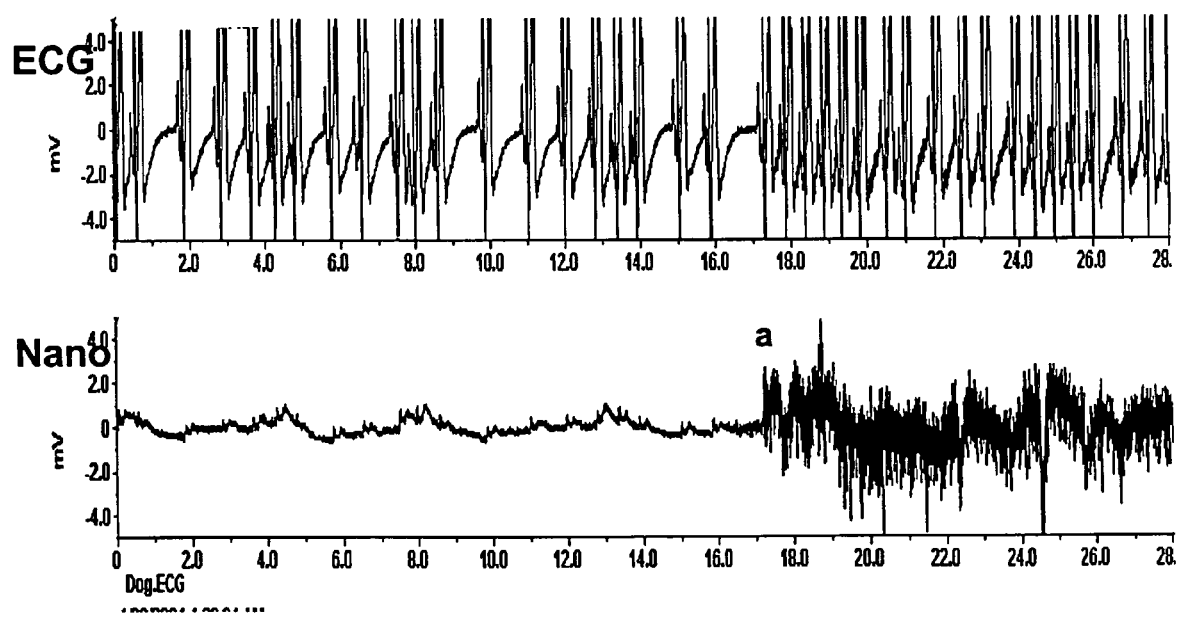
FIGS. 5A-C depict three separate simultaneous recordings of ECG and SGNA recorded from a nanoelectrode implanted at the LSG of an ambulatory normal canine subject over a time span of 28 seconds. The onset of increased SGNA (as designated by (a) through (h)) is followed by increased heart rate.
Figure 5B:
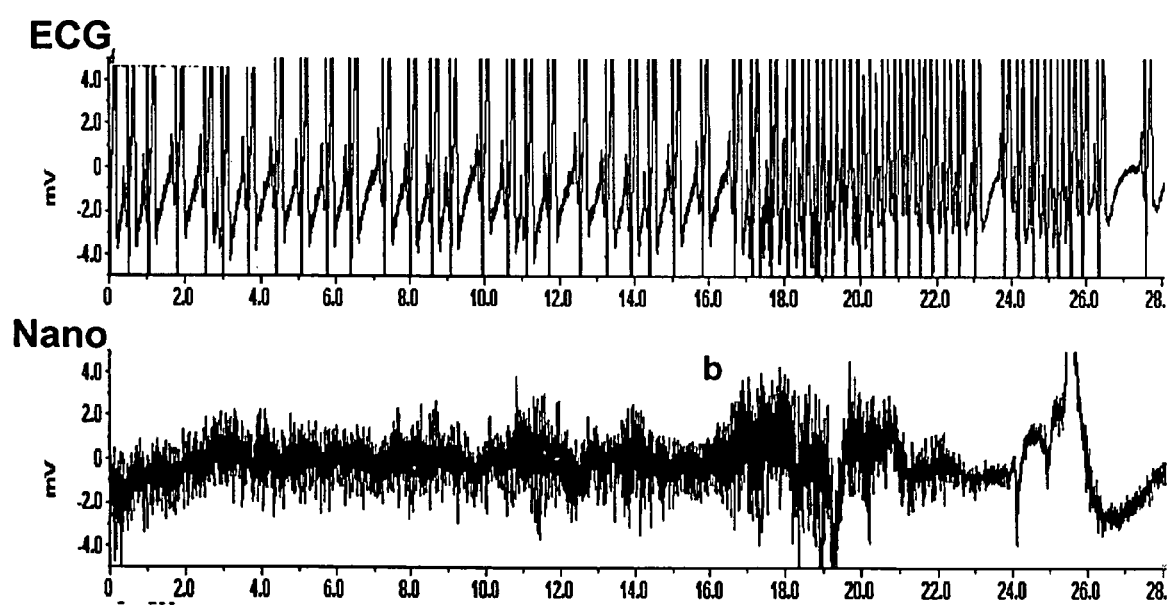
Figure 5C:
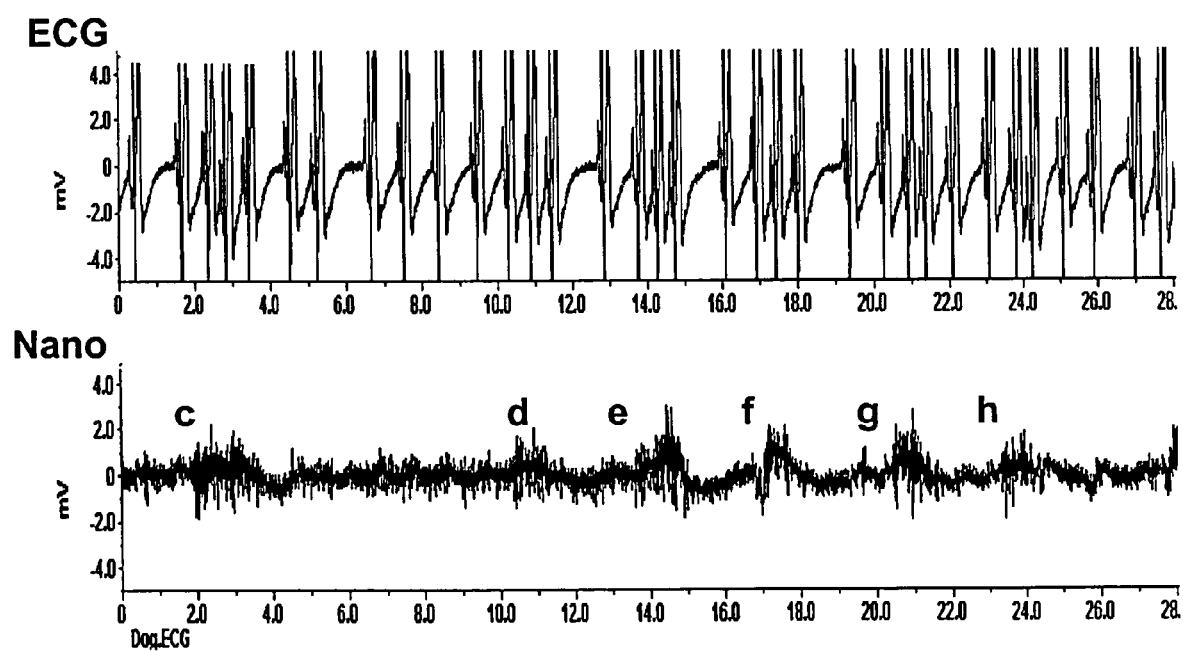

FIGS. 5A-C depict three separate simultaneous recordings of ECG and SGNA recorded from a nanoelectrode implanted at the LSG of an ambulatory normal canine subject over a time span of 28 seconds. The onset of increased SGNA (as designated by (a) through (h)) is followed by increased heart rate. FIG. 5A shows the onset of increased SGNA at time (a) which was followed by an increase in heart rate. FIG. 5B shows the increase in amplitude of the SGNA signals at (b) which is followed but further increases in heart rate. FIG. 5C shows burst increases in the amplitude of SGNA signals at (c), (d), (e), (f), (g), and (h), all of which were followed by short runs of increased atrial rate. This demonstrates that increased SGNA is causally related to increased heart rate.

Figure 6:
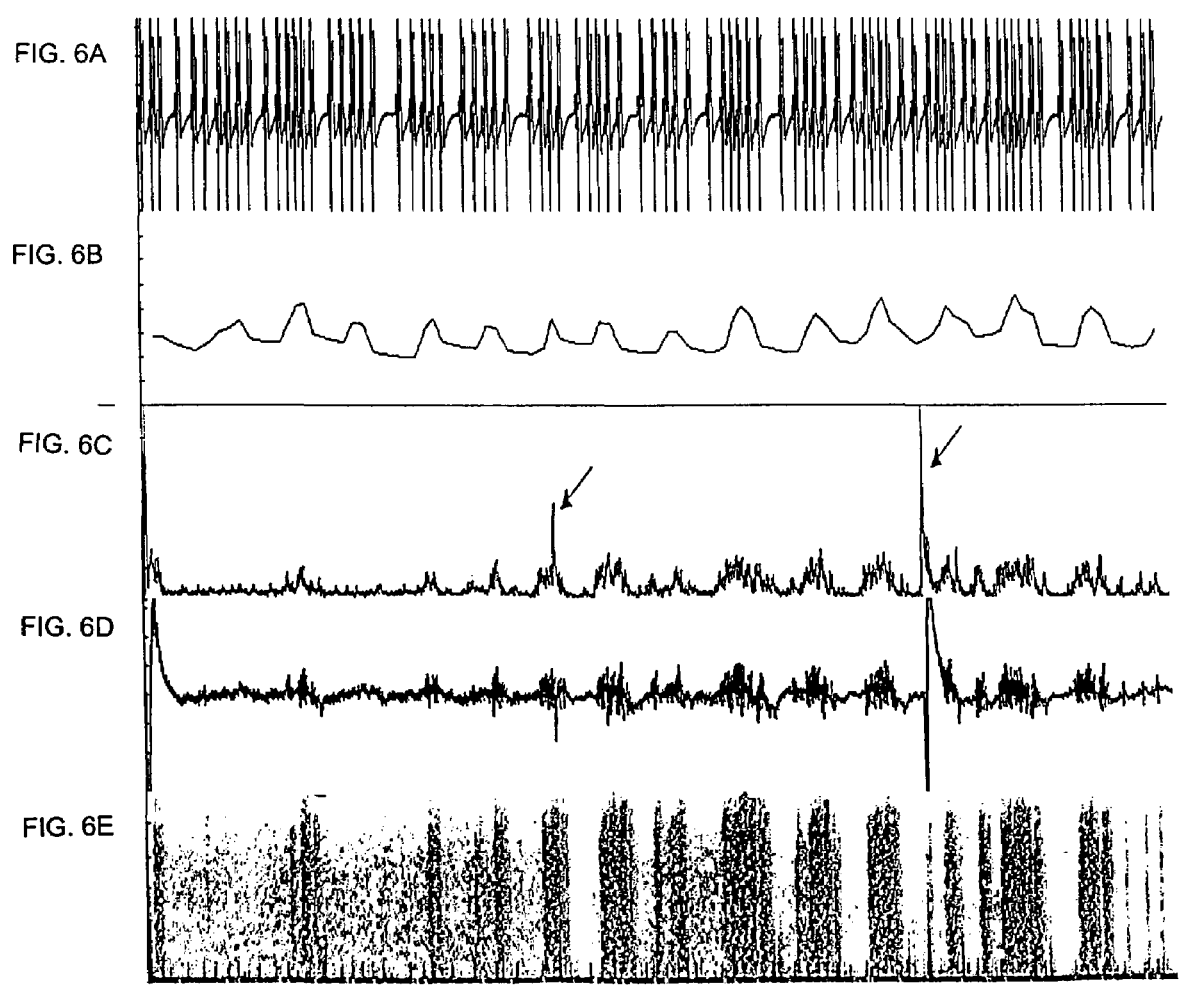
FIGS. 6A-E show the simultaneous 60 second recordings of (A) ECG, (B) the heart rate in beats per second, (C) the integrated SGNA, (D) the raw SGNA signals and (E) the sonogram (frequency in the Y-axis and power in shades of grey) obtained from an ambulatory normal canine subject.

FIGS. 6A-E shows a correlation between heart rate and the integrated SGNA. FIG. 6A depicts the ECG recording; FIG. 6B depicts the heart rate in beats per minute; FIG. 6C depicts the integrated nerve recording and FIG. 6D depicts the raw nerve signal and panel FIG. 6E depicts the sonogram. The frequency of the sonogram in panel FIG. 6E is provided in the Y axis and the power is indicated by the gray shading. A correlation is observed between the heart rate and integrated SGNA signal and between the heart rate and the sonogram.

Figure 7:
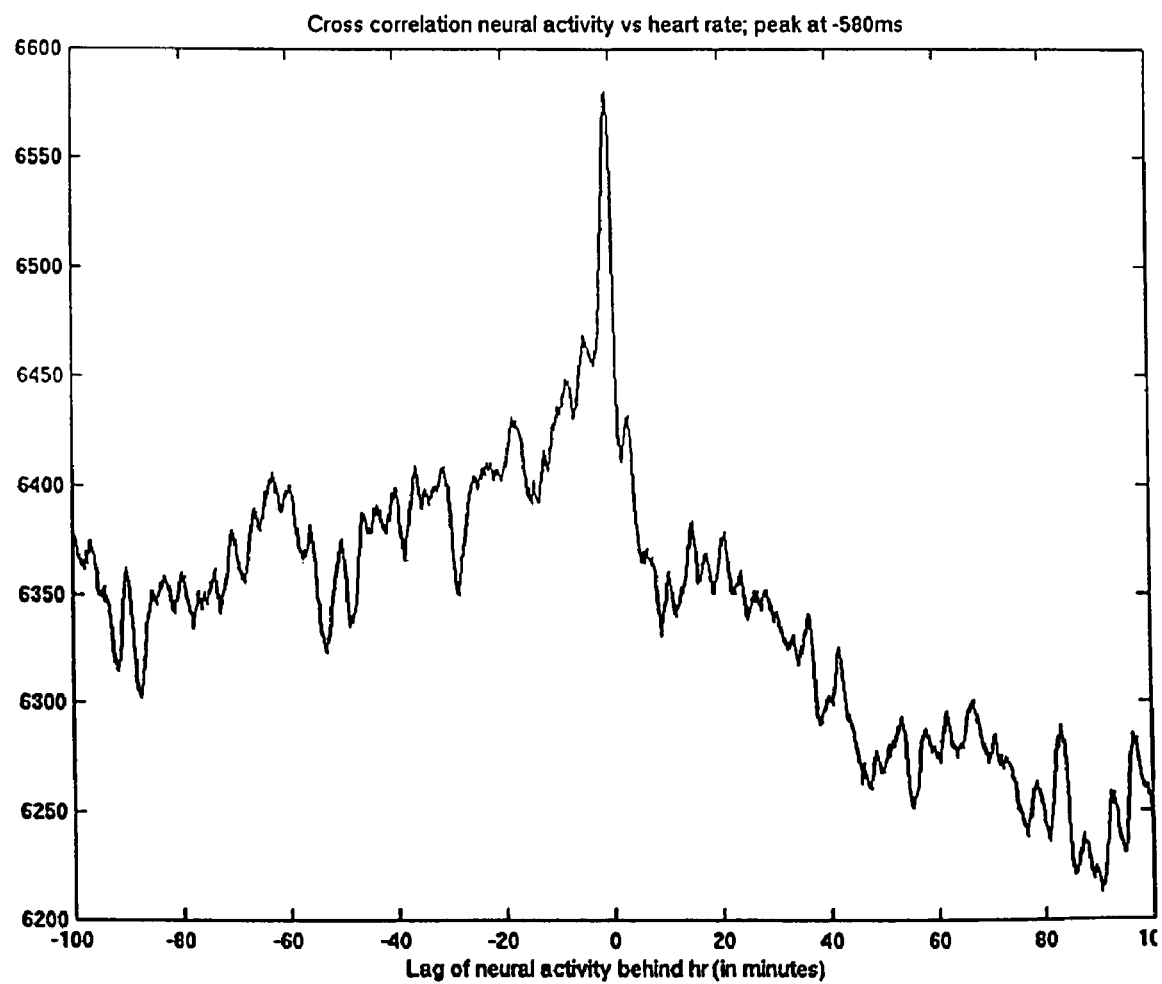
FIG. 7 shows the cross-correlation between SGNA and heart rate over a one hour period.

FIG. 7 depicts the cross-correlation between the SGNA and the heart rate over an hour. The onset of heart rate changes were defined by the S wave of the QRS complex. The peak correlation occurred at −580 ms, indicating that the increased sympathetic neural discharges is followed within 580 ms by an increased heart rate. The P waves occurred approximately 180 ms before the S wave on the QRS complex. Therefore, the increase in the SGNA occurred approximately 400 ms before the onset of the P wave.

EXAMPLE 3

Relationship between Sympathetic Neural Discharges and Heart Rate and Blood Pressure in Normal Canine Subjects Stellate ganglion nerve activity (SGNA) of six (6) purpose bred class-A adult mongrel dogs (18-25 kg) was monitored used to study the relationship between SGNA and heart rate and blood pressure; the diurnal variations of SGNA; and the effects of electrical stimulation of the stellate ganglia.

Sterile surgery was performed under general anesthesia. A DSI transmitter was used to record a total of 3 channels of electrograms. The sampling rate was 1,000/s and each of the biopontential channels had a bandwidth of 1-100 Hz and shared the same ground wires implanted in the subcutaneous pocket near the transmitter.

The DSI transmitter model D70-EEE was used for five of the canine subjects to record one channel of SGNA from the LSG, one channel of SGNA from the RSG and one channel of ECG. The recording electrodes were implanted under the fascia of the stellate ganglia and connected to a subcutaneous DSI transmitter to obtain continuous SGNA recordings. One pair of widely spaced bipolar wires was implanted to the subcutaneous tissues to record electrocardiogram. In one of the canine subjects, a nanoelectrode array was implanted under the fascia of the LSG for SGNA recordings and the nanoelectrode array was soldered to the stainless steel wires connected to the DSI transmitter. In the remaining canine subjects, the SGNA from the LSG and RSG were recorded using the bare wires that came with the DSI transmitter. FIG. 8A shows the strong correlation between the SGNA signals obtained from the LSG of a normal canine subject by nanoelectrode array and by stainless steel wire. An example of the actual SGNA recordings from the nanoelectrode and wire electrode is further depicted at the bottom of the bar graph. FIG. 8 demonstrates that SGNA may be adequately recorded using either the nanoelectrode array or the stainless steel wire electrode.

The DSI transmitter model D70-CCP was used for one canine subject to record one channel of SGNA from the LSG, one channel of ECG and one channel of blood pressure. In this canine subject, a blood pressure transducer was implanted into the descending aorta through a puncture hole in the left subclavian artery and the hole was then closed with a purse-string suture.

Manual and automated methods were used to examine the data obtained from the DSI transmitter. Manual analyses were used for short (up to 10 minute) segments of unprocessed raw data to correlate the sympathetic discharges with changes in blood pressure and heart rate. Automated analyses were performed using custom written software. During offline analysis, the sampled SGNA signal was digitally filtered between 25 and 150 Hz with an 8th order elliptical band-pass filter implemented in MATLAB (Mathworks, Natick, Mass.). The resulting signal was then full-wave rectified. A scalar value representing the average level of the SGNA was derived from the average value of this rectified and filtered signal.

Figure 9:
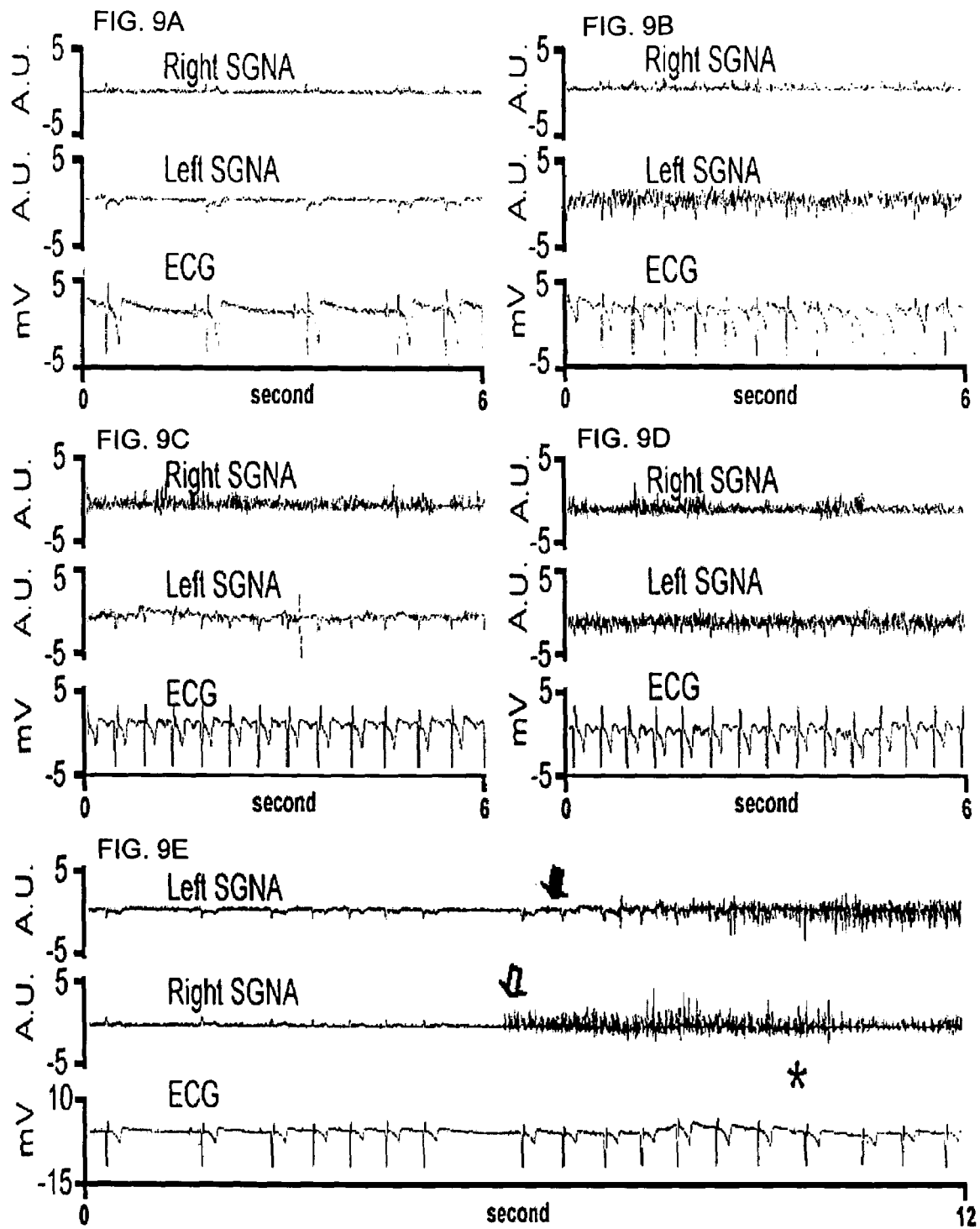
FIGS. 9A-E show the relationship between the SGNA (as a function of time and artificial units A.U.) and heart rate (as a function of time and mV) in an ambulatory normal canine subject.

The successful recording of SGNA is confirmed by a strong relationship between the signals registered from the stellate ganglia and the heart rate responses in all canine subjects studied. FIGS. 9A-E show continuous tracings of SGNA recordings from the RSG and the LSG and the concurrent electrocardiogram (ECG) from a normal canine subject. FIG. 9A show the baseline SGNA recording, which shows the absence of SGNA from the RSG and LSG, and the concurrent ECG, which shows a slow heart rate with significant sinus arrhythmia. FIGS. 9B-D show the increased SGNA recordings during rapid heart rate. Specifically, rapid heart rate is associated with increased left SGNA and sporadic right SGNA (FIG. 9B), increased right SGNA and sporadic left SGNA (FIG. 9C) and increased bilateral (left and right) SGNA (FIG. 9D).

FIG. 9E shows the onset of bilateral SGNA, followed by an increase in the heart rate. As further observed in FIG. 9E, the onset of the right SGNA preceded the onset of the left SGNA (as indicated by the arrows) and gradual deceleration and significant irregularity were observed in the heart rate (as indicated by the asterisk) in spite of continued bilateral SGNA. Similar results were demonstrated in one hundred randomly selected episodes of SGNA onset from three normal canine subjects with bilateral SGNA recordings, in which 90% were bilateral SGNA episodes where the right SGNA preceded the left SGNA by 300-900 ms and 10% were unilateral SGNA episodes.

Figure 10:
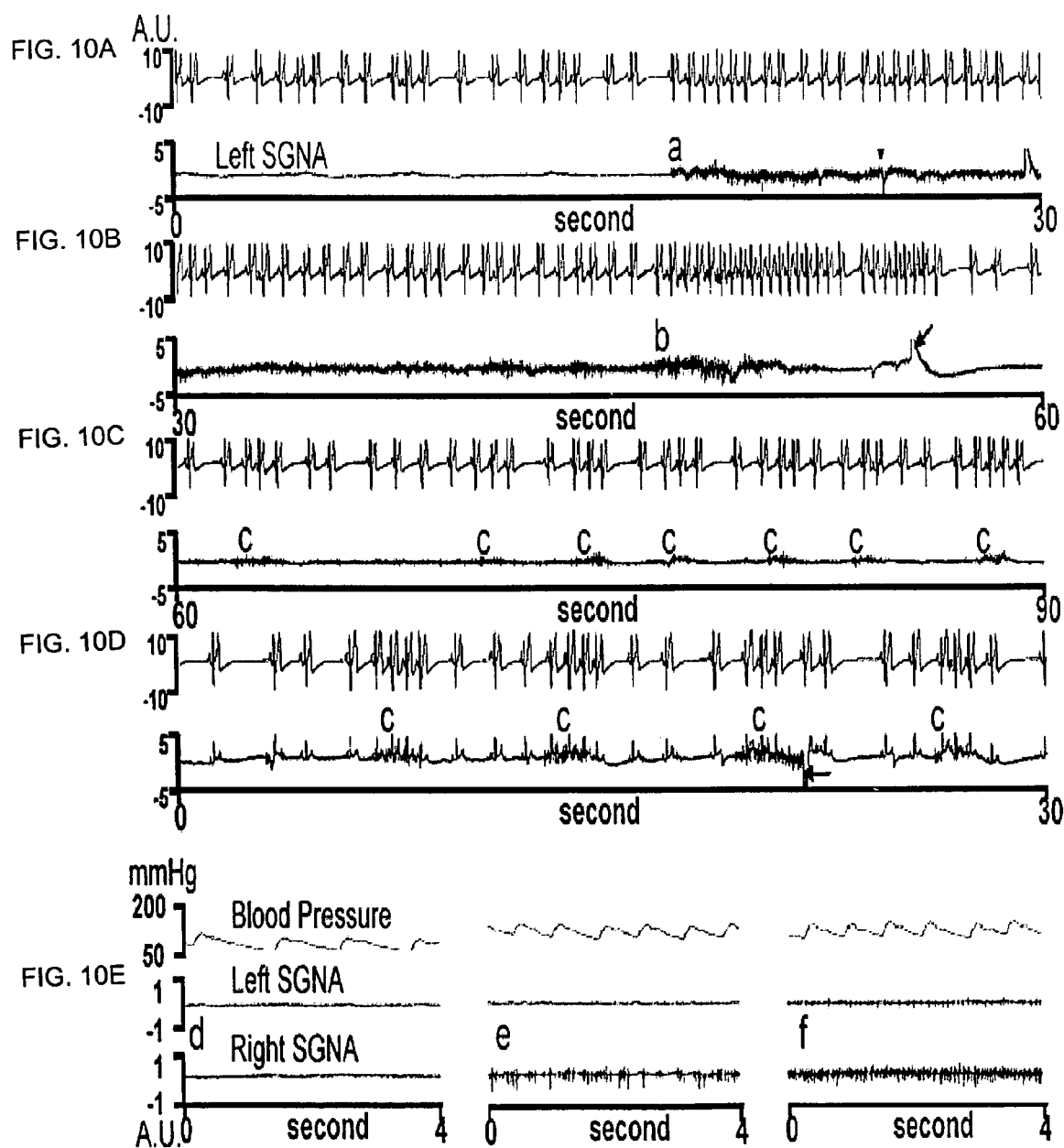
FIGS. 10A-E show the relationship between the SGNA from the LSG and heart rate and blood pressure.

The relationship between SGNA from the LSG and the heart rate are further demonstrated in the continuous recordings of heart rate, blood pressure and SGNA from the LSG in a normal canine subject, as shown in FIGS. 10A-E. FIGS. 10A-C are continuous recordings obtained from an ambulatory normal canine subject fifteen (15) days after implantation of the stainless steel wire electrode. In FIG. 10A, the increase in SGNA at (a) was followed by an increase in heart rate. In FIG. 10B, further increases in SGNA at (b) resulted in further increases in heart rate. In FIGS. 10C-D, brief bursts of SGNA at (c) were followed by immediate acceleration in heart rate. The arrows point to possible motion artifacts. FIG. 10E show the relationship between SGNA and blood pressure at baseline (d), unilateral increase in SGNA from the RSG at (e) and bilateral increase in SGNA from both the LSG and RSG at (f). Again, a stainless steel wire electrode was used to obtain the SGNA recordings.

EXAMPLE 4

Diurnal Variations in SGNA and Heart Rate in Normal Canine Subjects

There is a circadian variation of the incidence of sudden cardiac death. One possible explanation for this circadian variation may be the pattern of sympathetic activity. High sympathetic tone in the daytime may trigger the onset of ventricular arrhythmia. This is supported by the finding that circadian variation of sudden cardiac death or fatal myocardial infarction is substantially eliminated by administering propanolol in patients with heart disease and complex ventricular arrhythmia. Arrow W S, et al.: Circadian variation of sudden cardiac death or fatal myocardial infarction is abolished by propanolol in patients with heart disease and complex ventricular arrhythmias. Am. J. Cardiol. 1994; 74:816-821.

Diurnal variations of SGNA were studied by analyzing the SGNA recordings from the LSG and RSG of normal ambulatory canine subjects. The SGNA recordings obtained from the canine subjects were filtered to eliminate artifacts and far field ECG signals. The filtered SGNA signals were then subjected to automated analyses to determine the SGNA amplitude. Data from one week of continuous SGNA recordings were pooled together and averaged for each hour of the day. The SGNA recordings were then normalized to the SGNA recording at hour 0 (midnight).

FIGS. 11A-B shows the averaged hourly heart rate and SGNA (as a ratio to the SGNA at hour 0), respectively, at baseline plotted over a 24 hour period in six normal canine subjects. A statistically significant diurnal variation was present during the 24 hours for both heart rate and SGNA recordings. ANOVA showed a significant difference during the 24 hour period for both heart rate and SGNA. The orthogonal polynomials were then computed. The natural polynomial for a simple diurnal pattern is quadratic. For the heart rate variable, the quadratic term accounted for 79% of the between time sum of squares and the quadratic term for the SGNA accounted for 70% of the between time sum of squares.

EXAMPLE 5

Effect of Electrical Stimulation of the Stellate Ganglia in Normal Canine Subjects Upon completion of the drug tests, the canine subjects were anesthetized with isofluorane. The subcutaneous pocket was opened and the electrical wires leading to the stellate ganglion were cut. These wires were used for electrical stimulation and for recording SGNA using a Prucka Cardiolab system. The signals were acquired at 979 samples per second. The high pass and low pass filter settings were 30 and 500 Hz, respectively. A catheter in the femoral artery was used for monitoring blood pressure. After baseline SGNA, surface ECG and femoral blood pressure was measured simultaneously for a 30 minute period, electrical stimulation (5-50 mA, 5 ms pulse width at 20 Hz) was applied for 30 seconds through the implanted wires to the stellate ganglia.

Figure 12:
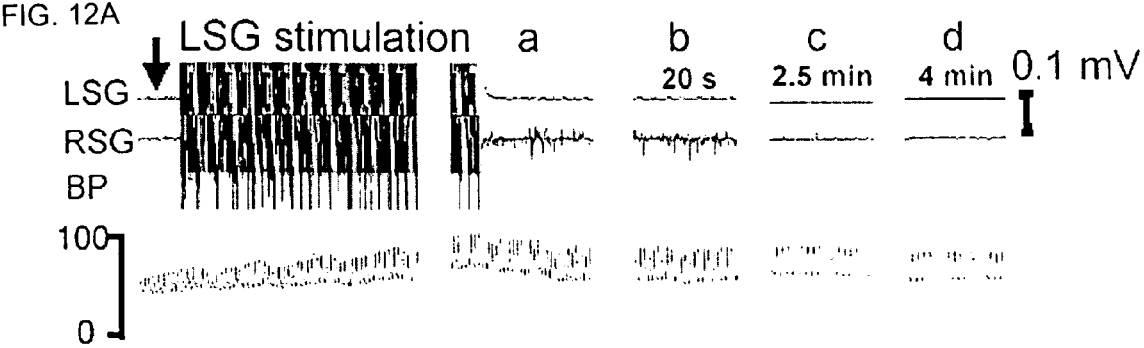
FIGS. 12A-C show the effect of electrical stimulation of the LSG and RSG in an ambulatory normal canine subject.
Figure 12:
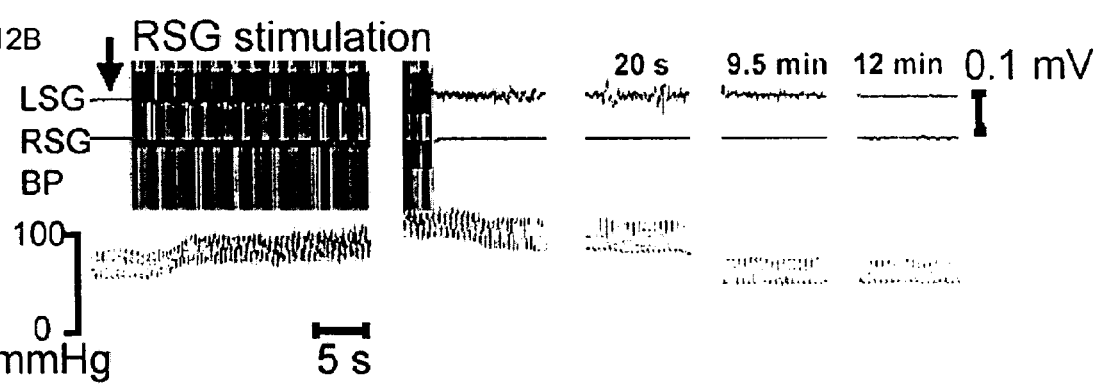
Figure 12:
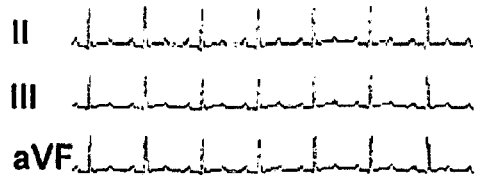
Figure 12:
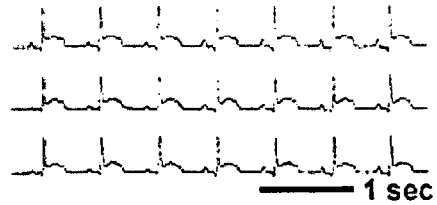

Electrical stimulation of the stellate ganglia resulted in abrupt increases in heart rate and blood pressure in all normal canine subjects. FIG. 12 shows the effects of electrical stimulation in one canine subject. No spontaneous SGNA was observed before commencement of electrical stimulation. LSG and RSG stimulation resulted in significantly increased blood pressure which persisted after electrical stimulation. As shown in FIG. 12A, a 50 mA current administered to the LSG resulted in an immediate increase in blood pressure, whereas in FIG. 12B, a 50 mA current administered to the RSG resulted in an increase in blood pressure within about 5 seconds.

At the end of the electrical stimulation, the stimulated stellate ganglion showed no electrical activity, but the contralateral stellate ganglion showed continuous discharges associated with persistently elevated blood pressure and heart rate. These discharges may persist from 3 to 20 minutes and suggest that the LSG and RSG communicate with each other through synapses in the spinal cord. These findings are also consistent with the observation that the SGNA from the LSG and RSG usually occur together, although the SGNA from the RSG may precede earlier than the SGNA from the LSG in most cases.

As shown in FIG. 12C, transient ST segment elevation in the recorded ECG was also observed during electrical stimulation, indicating significant myocardial ischemia, probably as a combined result of alpha-receptor induced coronary constriction and beta-receptor mediated increase in oxygen consumption.

In two of the three canine subjects with bilateral SGNA recordings, electrical stimulation of the stellate ganglion on one side resulted in persistent SGNA of the contralateral stellate ganglion. In other words, electrical stimulation of the stellate ganglion on one side resulted in persistent SGNA of the contraleteral stellate ganglion.

EXAMPLE 6

Effect of Drug Perturbations on SGNA in Normal Canine Subjects

Beta-blocker (nadolol) therapy was administered to all six normal canine subjects. The results showed that the averaged heart rate reduced from 99+8 bpm at baseline to 88+9 bpm during nadolol therapy (n=6, p=0.001). Heart rate reduction was observed in all six canine subjects studied. However, the averaged SGNA from the LSG during nadolol therapy as a ratio of baseline SGNA was 0.96+0.09 (n=6, p=0.07).

Nitroprusside was also administered to the canine subjects via intravenous line infusion and resulted in transient reduction in blood pressure and a modest increase in SGNA. Phenylephrine infusion was observed to increase blood pressure and decrease SGNA. Thus, SGNA was higher during nitroprusside infusion as compared to during phenylephrine infusion.

EXAMPLE 7

Relationship between SNGA and VT, VF and SCD in Canine Models for SCD

Continuous sympathetic nerve recordings were also obtained from four (4) canine models for sudden cardiac death. A canine model for sudden cardiac death is disclosed in U.S. Pat. No. 6,351,668, which is incorporated herein by reference. The circumstances under which sudden cardiac death occurs in canine subjects are similar to circumstances under which sudden cardiac death occurs in human patients. Accordingly, a canine SCD model may be used to analyze and identify conditions within the heart leading up to a ventricular tachycardia or ventricular fibrillation of the type leading to sudden cardiac death, as disclosed in U.S. Pat. No. 6,353,757, which is incorporated herein by reference. A canine SCD model may also be used to develop and test the effectiveness of new techniques for preventing a ventricular tachycardia, ventricular fibrillation or sudden cardiac death from occurring, as disclosed in U.S. Pat. No. 6,398,800 and pending U.S. application Ser. No. 10/033,400, filed Dec. 12, 2001, which are incorporated herein by reference.

The canine SCD model is created by inducing myocardial hyperinnervation within the LSG in combination with creating a complete atrioventricular (AV) block and inducing a relatively mild myocardial infarction (MI). The AV block is typically created by ablating the AV node of the heart using an ablation catheter and the MI is induced by ligating the left anterior descending portion of the coronary artery. Myocardial hyperinnervation is stimulated by application of nerve growth factor (NGF) or other neurotrophic vectors to the LSG. Alternatively, electrical stimulation signals may be applied to the LSG.

By creating an AV block and by inducing an MI within the heart of an adult canine test subject, and then by stimulating nerve growth within the LSG of the subject using NGF, a significant increase in the likelihood of SCD arising from phase two ventricular arrhythmias has been observed. Thus, the method permits SCD to be induced within test animals in a manner facilitating the collection of data pertinent to conditions within the heart arising prior to SCD and for testing techniques intended to prevent phase two VT and VF within patients subject to a previous MI.

In the SCD model canine subjects, SGNA recordings from the LSG were obtained from the stainless steel wires of the DSI model D70-EEE transmitter implanted under the fascia of the LSG. ECG recordings were obtained by connecting two biopotential channels of the DSI transmitter to local left ventricle and left atrial recordings, respectively.

Figure 13:
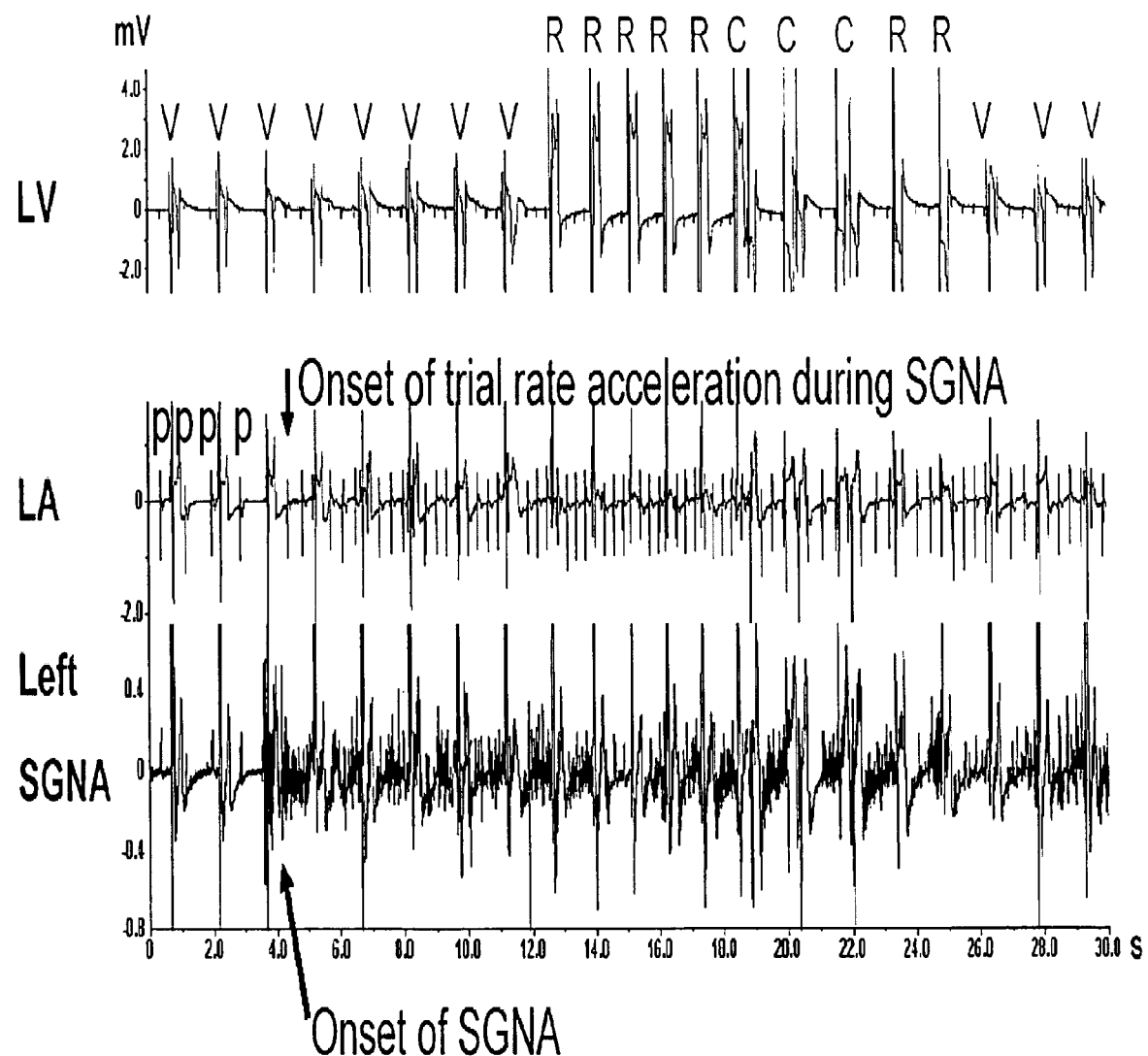
FIG. 13 is a 30 second simultaneous bipolar left ventricle (LV) and left atrial (LA) electrogram and SGNA using a stainless steel wire electrode implanted in the LSG of a canine SCD model (complete atrioventricular block, myocardial infarction and nerve growth factor infusion to the LSG) taken four weeks after surgery. Before the onset of increased SGNA, the ventricles were paced at 40 bpm (V) while there was dissociated sinus rhythm (P). The onset of increased SGNA was followed by abrupt increase in atrial rate and the development of ventricular escape rhythm (R) and 3 couplets (C).

FIG. 13 is a 30 second recording of SGNA from the LSG in a SCD canine model. This recording was taken four weeks after the first surgery. Bipolar left ventricle (LV) and left atrial (LA) electrograms were recorded simultaneously with left SGNA. Before the onset of left SGNA, the ventricles were paced at 40 bpm (V) while there was dissociated sinus rhythm (P). The onset of left SGNA was followed by an abrupt increase of atrial rate and the development of a ventricular escape rhythm (R) and three couplets (C).

Figure 14:
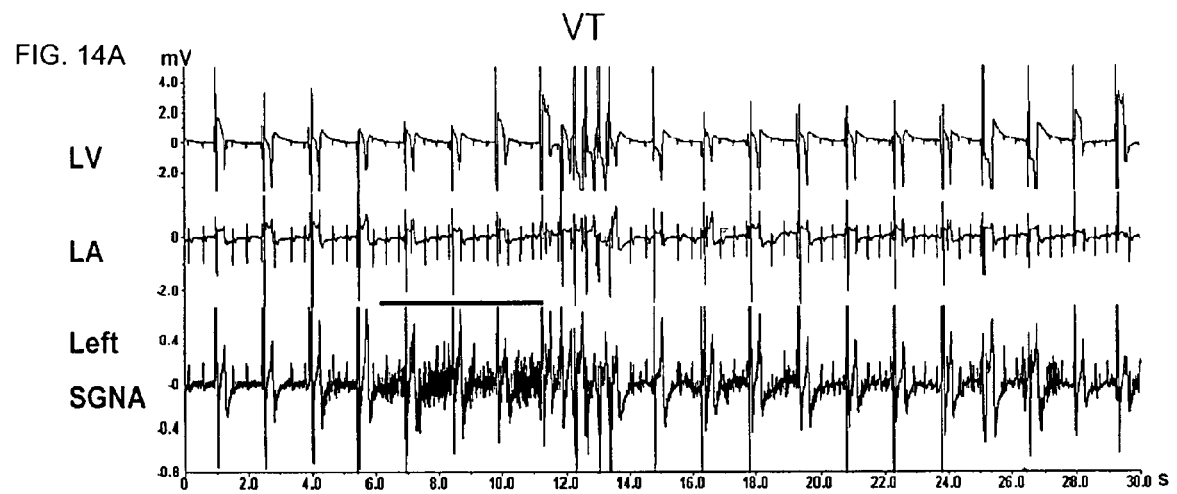
FIGS. 14A-B show two separate 30 second bipolar LV and LA electrograms and SGNA obtained by a stainless steel wire electrode implanted in the LSG of an ambulatory canine SCD model taken four weeks after surgery.
Figure 14:
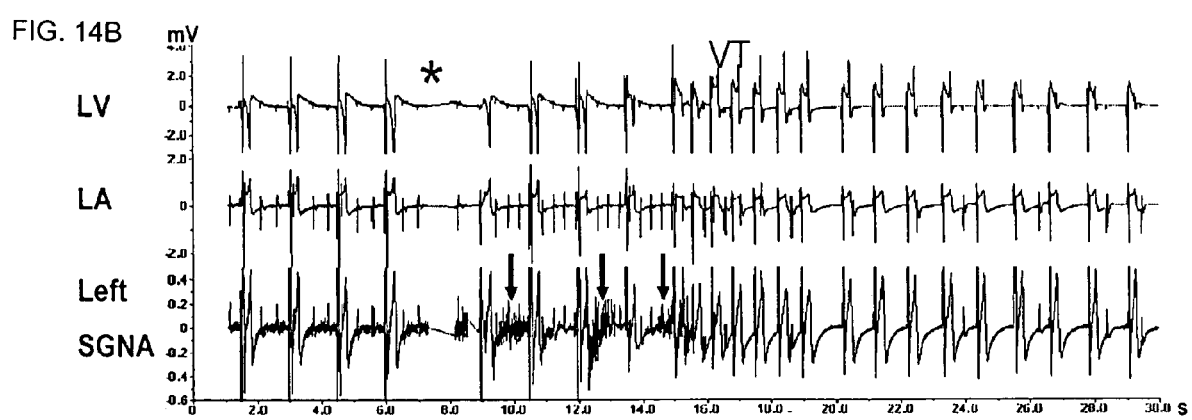

An increase in SGNA from the LSG was observed to precede the onset of ventricular tachycardia, ventricular fibrillation and sudden cardiac death. FIGS. 14A-B are simultaneous 30 second recordings of SGNA from the LSG and ECG in a canine SCD model taken four weeks after the first surgery. FIG. 14A shows the onset of ventricular tachycardia following either persistent SGNA, as indicated by the horizontal line above the SGNA recordings. The onset of ventricular tachycardia also induced by intermittent SGNA, as indicated by the arrows in FIG. 14B. Increased SGNA from the LSG induced VT after a 6 second latency. The asterisk in FIG. 14B shows a signal drop, likely due to the movement of the SCD canine subject.

Figure 15:
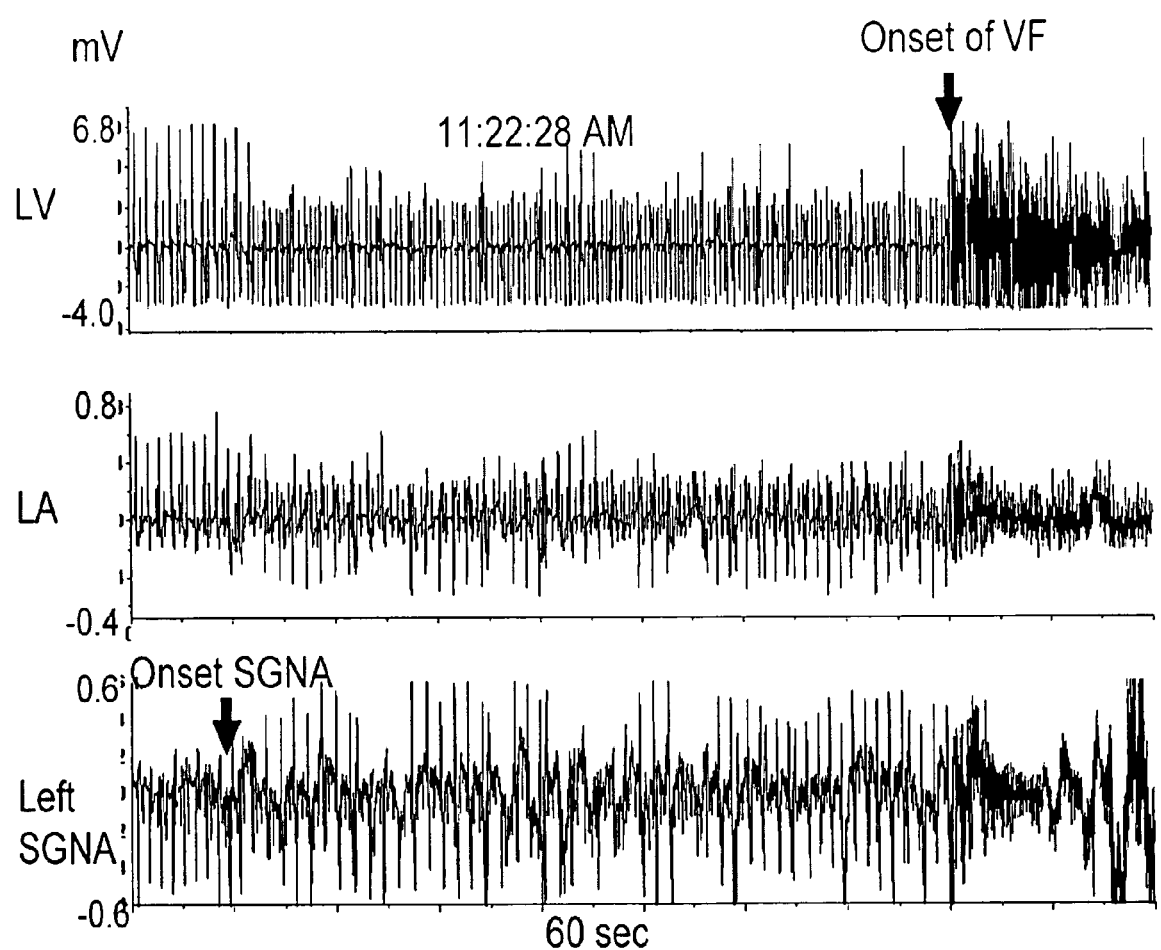
FIG. 15 shows a 60 second bipolar LV and LA electrograms and SGNA obtained by a stainless steel wire electrode implanted in the LSG of a canine SCD model. The LV recording showed accelerated escape rate and reduced electrogram amplitude soon after the onset of SGNA. The onset of increased SGNA (as indicated by the arrow) was followed by ventricular fibrillation after approximately 40 seconds.

The relationship between elevated SGNA from the LSG and heart rate is depicted in FIG. 15, which shows a 60 second bipolar LV and LA electrograms and SGNA obtained by a stainless steel wire electrode implanted in the LSG of a canine SCD model. The LV recording showed accelerated escape rate and reduced electrogram amplitude soon after the onset of SGNA. The onset of increased SGNA (as indicated by the arrow) was followed by ventricular fibrillation after approximately 40 seconds.

Figure 16:
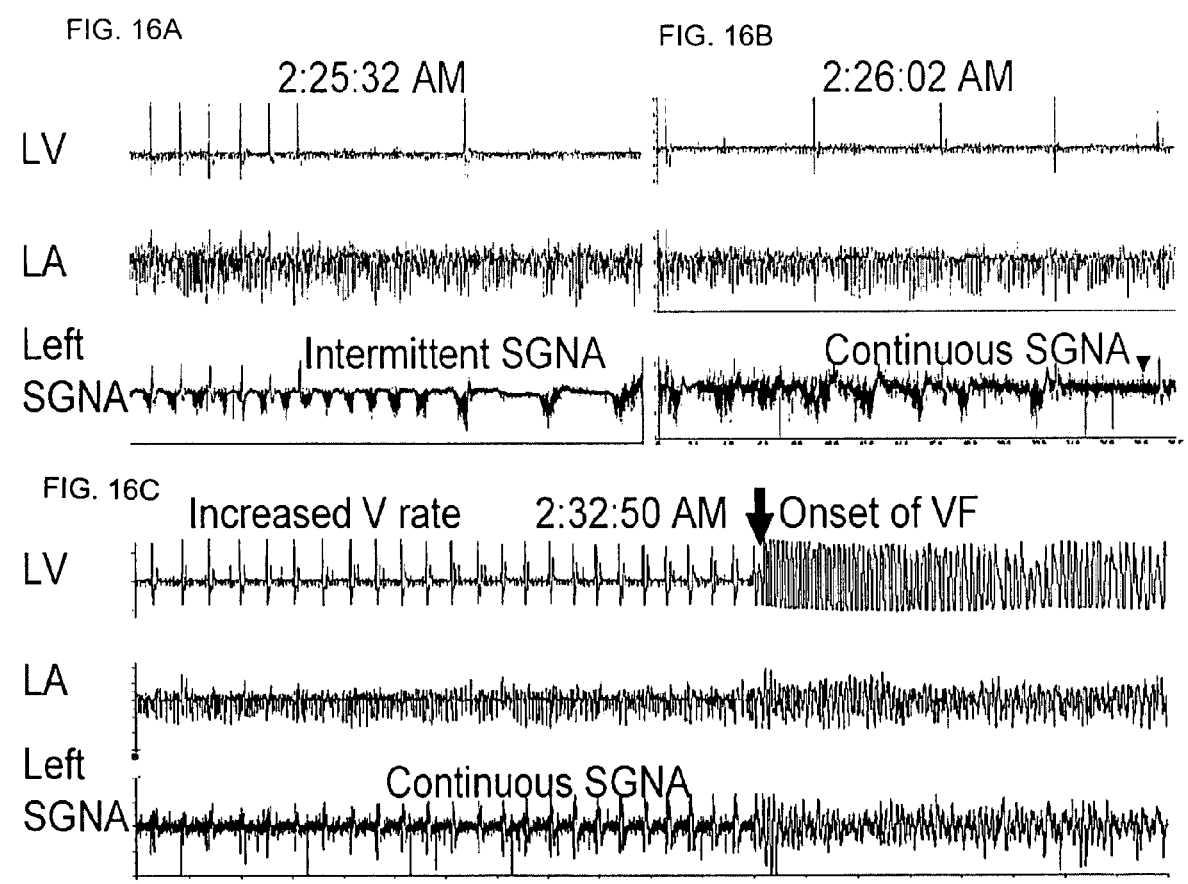
FIGS. 16A-C show bipolar LV and LA electrograms and SGNA obtained by a stainless steel wire electrode implanted in the LSG of a canine SCD model.
Figure 17:
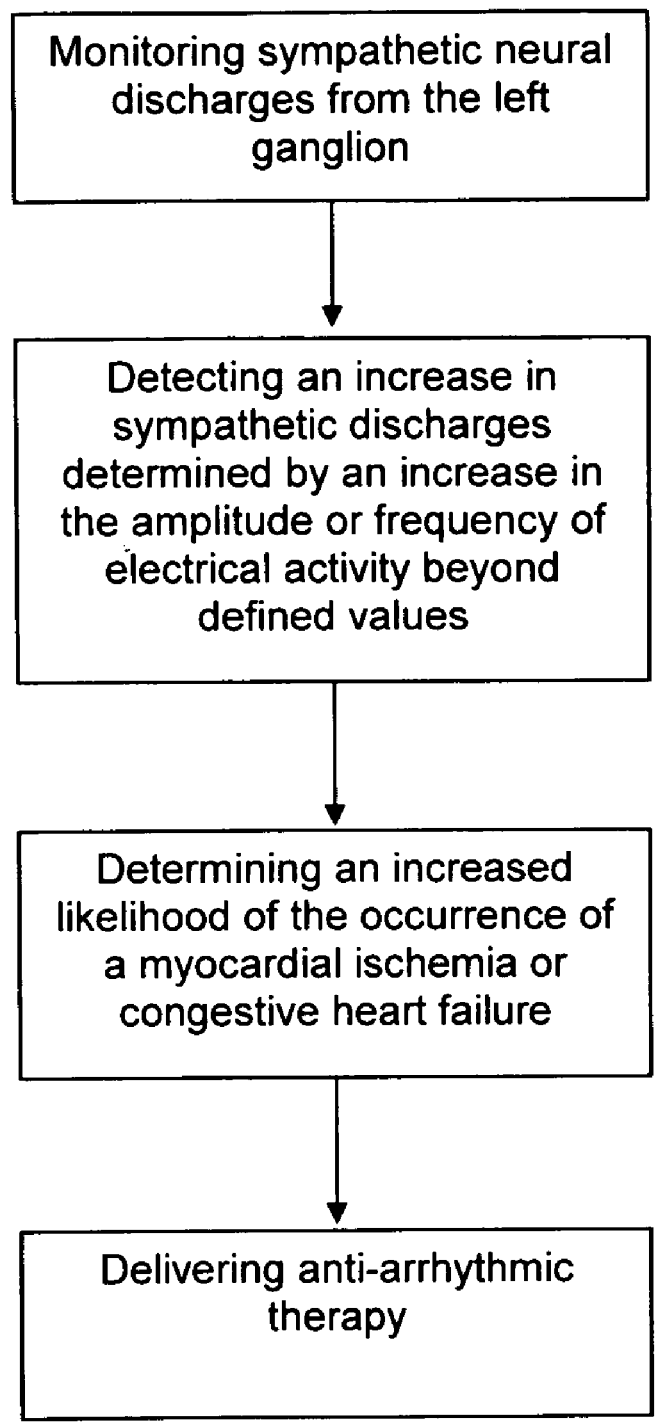
FIG. 17 is in the form of a flow chart showing a method for determining an increased likelihood of the occurrence of myocardial ischemia or congestive heart failure.

FIGS. 16A-C show bipolar LV and LA electrograms and SGNA obtained by a stainless steel wire electrode implanted in the LSG of a canine SCD model. FIG. 16A shows pacemaker non-capture, resulting in the conversion of intermittent SGNA into continuous SGNA in FIG. 16B. The SGNA continued uninterrupted for 6 minutes, resulting in accelerated ventricular escape rhythm followed by ventricular fibrillation, as shown in FIG. 16C. FIGS. 16A-B are continuous tracings.

EXAMPLE 8

Effects of Anti-convulsants on SGNA

Anti-convulsant drugs may exert an anti-arrhythmic effect by suppressing the high frequency SGNA from the LSG. Phenytoin (Dilantin®) is one of the most commonly used anti-convulsants and has been shown to suppress the SGNA in ambulatory canine subjects within the therapeutic range of 10-20 mg/L.

After confirming the successful recording of SGNA from the canine subject, 400 mg (approximately 18 mg/kg) of phenytoin was administered intravenously to the canine subject. Phenytoin was injected at 9:45 a.m. and the tracings following that time show the effects of phenytoin injection on the heart rate and the SGNA of the canine subject.

The serum concentration of the canine subject two hours after the initial injection was 12.9 mg/L, which was within the therapeutic range of 10-20 mg/L. The results showed that SGNA appeared to decrease significantly 3-12 hours after the initial injection. There was an increase in the SGNA observed roughly 20 hours after the initial injection, which may represent a rebound sympathetic neural discharges hyper-activation.

An oral dose of phenytoin was also administered to the canine subject (800 mg single dose, or roughly 30 mg/kg) after serum levels from the initial injection of phenytoin dropped to zero. The serum level 2 hours after the oral dose was 2.2 mg/L, which is sub-therapeutic. At this dose, there were little changes in the SGNA. These data show that a therapeutic dose of phenytoin can suppress SGNA from the LSG and that a sub-therapeutic dose has little effect. The data also suggest that a dose-response relationship may be present.

What is claimed:

1. A method for determining an increased likelihood of the occurrence of a myocardial ischemia or congestive heart failure, the method comprising:
    monitoring the left stellate ganglia nerve activity of the patient; and
    detecting an increase in the left stellate ganglia nerve activity; and
    producing a radio-transmitted signal in response to a detected increase in the left stellate ganglia nerve activity.

2. The method of claim 1 wherein the step of monitoring the stellate ganglia nerve activity comprises implanting nanoelectrode array on the left stellate ganglion in the patient, wherein the nanoelectrode array senses the electrical activity of the left stellate ganglion.

3. The method of claim 2 wherein the increase in the left stellate ganglia nerve activity is determined by an increase in the amplitude and/or frequency of the sensed electrical activity beyond a two fold increase of defined normal values.

4. The method of claim 2 wherein the increase in the left stellate ganglia nerve activity is determined by comparing the monitored electrical activity and the normal electrical activity of the patient.

5. The method of claim 4 wherein the output signal is an audible sound.

6. The method of claim 5 further comprising the step of delivering therapy in response to a radio-transmitted signal, the therapy selected from any one or more of the group consisting of: delivering one or more pharmacological agents; stimulating myocardial hyperinnervation in the sinus node and right ventricle of the heart of the patient; and applying cardiac pacing, cardioversion or defibrillation shocks.

7. The method of claim 6 wherein the one or more pharmacological agents is an anti-convulsant agent.

8. The method of claim 7 wherein the anti-convulsant agent is selected from the group consisting of: phenytoin, carbamazepine, valproate, and phenobarbitone.

9. The method of claim 6 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

10. A system for determining an increased likelihood of the occurrence of a myocardial ischemia or congestive heart failure, the system comprising:
    a nanoelectrode array sensor for acquiring data relating to the sympathetic neural discharges of a patient from the stellate ganglia or the thoracic ganglia;
    a processor programmed to receive the data acquired from the nanoelectrode array sensor, wherein the processor analyzes the data and determines if there is an increase in the sympathetic neural discharge; and
    an output unit for generating a radio transmitted output signal in response to a determined increase in the sympathetic neural discharge.

11. The system of claim 10 wherein the nanoelectrode array sensor is an electrode that is implanted on the left stellate ganglion of the patient and wherein the electrode senses the electrical activity of the left stellate ganglion.

12. The system of claim 11 wherein the processor determines that an increase in the sympathetic neural discharge has occurred by an increase in the amplitude or frequency of the sensed electrical activity beyond a two fold increase defined normal values.

13. The system of claim 11 wherein the processor determines that an increase in the sympathetic neural discharge has occurred by comparing the sensed electrical activity and the normal electrical activity of the left stellate ganglion.

14. The system of claim 10 wherein the output signal is an audible sound.

15. The system of claim 10 wherein the output signal is a radio-transmitted signal.

16. The system of claim 15 further comprising delivery module for delivering therapy in response to the radio-transmitted signal, the therapy selected from any one or more of the group consisting of: delivering one or more pharmacological agents; stimulating myocardial hyperinnervation in the sinus node and right ventricle of the heart of the patient; and applying cardiac pacing, and cardioversion or defibrillation shocks.

17. The system of claim 16 wherein the one or more pharmacological agents is an anti-convulsant agent.

18. The system of claim 17 wherein the anti-convulsant agent is selected from the group consisting of: phenytoin, carbamazepine, valproate, and phenobarbitone.

19. The system of claim 16 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

20. A system for determining an increased likelihood of the occurrence of a myocardial ischemia or congestive heart failure associated with elevated sympathetic neural discharges in a patient, the system comprising:
    means for monitoring the sympathetic neural discharges of a patient from the left stellate ganglia or the thoracic ganglia;
    means for determining an increase in the sympathetic neural discharge; and
    means for producing an output signal in response to a determined increase in the sympathetic neural discharge.

21. The system of claim 20 wherein the means for monitoring sympathetic neural discharges comprises sensing the electrical activity of the left stellate ganglion using a nanoelectrode array.

22. The system of claim 21 wherein the means for determining an increase in the sympathetic neural discharges comprises comparing the sensed electrical activity of the left stellate ganglion and the normal electrical activity of the left stellate ganglion.

23. The system of claim 21 wherein the increase in the sympathetic neural discharge is determined by detecting an increase in the amplitude or frequency of the sensed electrical activity beyond a two fold increase of defined normal values.

24. The system of claim 20 wherein the output signal is an audible sound.

25. The system of claim 20 wherein the output signal is a radio-transmitted signal.

26. The system of claim 25 further comprising means for delivering therapy in response to the radio-transmitted signal, the therapy selected from any one or more of the group consisting of: delivering one or more pharmacological agents; stimulating myocardial hyperinnervation in the sinus node and right ventricle of the heart of the patient; and applying cardiac pacing, cardioversion or defibrillation shocks.

27. The system of claim 26 wherein the one or more pharmacological agents is an anti-convulsant agent.

28. The system of claim 27 wherein the anti-convulsant agent is selected from the group consisting of: phenytoin, carbamazepine, valproate, and phenobarbitone.

29. The system of claim 26 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

30. A method for determining an increased likelihood of the occurrence of a myocardial isehemia or congestive heart failure, the method comprising:
monitoring the left stellate ganglia nerve activity of the patient by means of an implanted electrode on the left stellate ganglia of a patient;
detecting an increase in the left stellate ganglia nerve activity; and
producing a radio-transmitted signal in response to a detected increase in the left stellate ganglia nerve activity.

31. The method of claim 30 further comprising the step of delivering therapy in response to the radio-transmitted signal, the therapy selected from any one or more of the group consisting of: delivering one or more pharmacological agents; stimulating myocardial hyperinnervation in the sinus node and right ventricle of the heart of the patient; and applying cardiac pacing, cardioversion or defibrillation shocks.

32. The method of claim 31 wherein the one or more pharmacological agents is an anti-convulsant agent.

33. The method of claim 32 wherein the anti-convulsant agent is selected from the group consisting of: phenytoin, carbamazepine, valproate, and phenobarbitone.

34. The method of claim 31 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

35. A system for determining an increased likelihood of the occurrence of a myocardial ischemia or congestive heart failure and other diseased condition of the heart associated with elevated sympathetic neural discharges in a patient, the system comprising:
a sensor configured to acquire data relating to the sympathetic neural discharges of a patient from the left stellate ganglia;
a processor programmed to receive the data acquired from the sensor, wherein the processor analyzes the data and determines if there is an increase in the sympathetic neural discharge; and
an output unit for generating a radio transmitted output signal in response to a determined increase in the sympathetic neural discharge.

36. The system of claim 35 further comprising a delivery module for delivering therapy in response to the command signal, the therapy selected from any one or more of the group consisting of: delivering one or more pharmacological agents; stimulating myocardial hyperinnervation in the sinus node and right ventricle of the heart of the patient; and applying cardiac pacing, and cardioversion or defibrillation shocks.

37. The system of claim 36 wherein the one or more pharmacological agents is an anti-convulsant agent.

38. The system of claim 37 wherein the anti-convulsant agent is selected from the group consisting of: phenytoin, carbamazepine, valproate, and phenobarbitone.

39. The system of claim 36 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

* * * * *